(12) United States Patent
Benson

(10) Patent No.: US 12,138,385 B2
(45) Date of Patent: Nov. 12, 2024

(54) AUTHENTICATABLE INHALATION SYSTEM

(71) Applicant: Eric R Benson, Gilbert, AZ (US)

(72) Inventor: Eric R Benson, Gilbert, AZ (US)

(*) Notice: Subject to any disclaimer, the term of this patent is extended or adjusted under 35 U.S.C. 154(b) by 1038 days.

(21) Appl. No.: 17/026,287

(22) Filed: Sep. 20, 2020

(65) Prior Publication Data

US 2021/0001063 A1     Jan. 7, 2021

Related U.S. Application Data

(60) Provisional application No. 62/903,301, filed on Sep. 20, 2019.

(51) Int. Cl.
*A61M 15/00*      (2006.01)
*G16H 20/13*      (2018.01)

(52) U.S. Cl.
CPC .... *A61M 15/0013* (2014.02); *A61M 15/0025* (2014.02); *A61M 15/0086* (2013.01); *G16H 20/13* (2018.01); *A61M 2205/583* (2013.01)

(58) Field of Classification Search
CPC ........ A24F 40/485; A24F 40/49; A24F 40/53; A24F 40/60; A24F 40/65; A24F 40/05; A24F 40/10; A24F 40/40; A24F 40/42; A24F 47/008; A24F 7/02; A61M 11/02; A61M 11/04; A61M 11/041; A61M 11/042; A61M 15/00; A61M 15/0001; A61M 15/0013; A61M 15/0016; A61M 15/0021; A61M 15/0025; A61M 15/0028; A61M 15/003; A61M 15/0033; A61M 15/0035;

(Continued)

(56) References Cited

U.S. PATENT DOCUMENTS

| | | | |
|---|---|---|---|
| 6,513,524 B1* | 2/2003 | Storz | A61M 16/208 128/203.29 |
| 8,955,522 B1* | 2/2015 | Bowen | A24F 40/42 131/273 |

(Continued)

FOREIGN PATENT DOCUMENTS

| | | | | |
|---|---|---|---|---|
| KR | 20160110670 A | * | 9/2016 | A24F 15/01 |
| WO | WO-9416755 A1 | * | 8/1994 | A61M 15/00 |

(Continued)

*Primary Examiner* — Annette Dixon
(74) *Attorney, Agent, or Firm* — Barry Choobin; Patent 360

(57) ABSTRACT

An inhalation system including a fluid transfer member, a valve member, a cartridge assembly, and a mouthpiece, and a method of use thereof are provided. The valve member connects to an open end of the fluid transfer member. The cartridge assembly, positioned within the valve member, includes a substance holder and an absorbent member accommodated within a cartridge for containing and absorbing an inhaling substance. When the valve member connects to a vaporizer, the vaporizer heats the absorbent member to vaporize and release an inhaling fluid into the fluid transfer member. When the valve member connects to the mouthpiece, the valve member receives and transfers the inhaling fluid vapor from the fluid transfer member to a user's mouth via the mouthpiece. The locking mouthpiece assembly allows authentication of the user prior to releasing the inhaling fluid to the user's mouth.

19 Claims, 22 Drawing Sheets

(58) Field of Classification Search
CPC .......... A61M 15/0041; A61M 15/0086; A61M 15/0096; A61M 15/06; A61M 16/0078; A61M 16/201; A61M 16/202; A61M 2205/07; A61M 2205/27; A61M 2205/276; A61M 2205/583; A61M 2205/3306; A61M 2205/3553; A61M 2205/3569; A61M 2205/3584; A61M 2205/3592; A61M 2205/502; A61M 2205/505; A61M 2205/60; A61M 2205/6063; A61M 2205/6072; A61M 2205/609; A61M 2205/8281; A61M 15/0036; A61M 15/0038; A61M 15/004; A61M 15/009; A61M 11/007; A61M 2025/0006; A61M 39/02; A61M 11/003; A61M 11/005; A61M 15/0008; A61M 15/002; A61M 15/0045; A61M 15/0066; A61M 15/0068; A61M 15/008; A61M 15/0081; A61M 15/0085; A61M 15/0088; A61M 16/20; A61M 16/208; A61M 2016/0018; A61M 2016/0027; A61M 2016/0039; A61M 2202/064; A61M 2205/0294; A61M 2205/17; A61M 2205/3334; A61M 2205/3653; A61M 2205/43; A61M 2205/50; A61M 2205/52; A61M 2205/587; A61M 2205/6018; A61M 2205/8206; A61M 2209/01; A61M 2209/045; G16H 20/10; G16H 20/13; G16H 40/63; G16H 40/67; A61B 5/1172; A61K 9/0075; A63B 2057/0018; A63B 2209/08; A63B 57/20; A63B 57/203; A63B 57/207; B01L 2200/025; B01L 2200/026; B01L 2200/027; B01L 2200/028; B01L 2200/04; B01L 2200/0668; B01L 2200/0684; B01L 2200/0689; B01L 2200/087; B01L 2200/10; B01L 2200/16; B01L 2300/023; B01L 2300/025; B01L 2300/04; B01L 2300/044; B01L 2300/06; B01L 2300/0627; B01L 2300/0645; B01L 2300/0681; B01L 2300/0816; B01L 2300/0838; B01L 2300/0864; B01L 2300/0867; B01L 2300/087; B01L 2300/12; B01L 2300/161; B01L 2300/1827; B01L 2400/0406; B01L 2400/0487; B01L 2400/0677; B01L 2400/0683; B01L 3/5027; B01L 3/502715; B01L 3/502723; B01L 3/502738; B01L 3/5029; B05D 2518/00; B05D 3/002; B06B 1/0651; B06B 2201/77; C12Q 1/6825; F04D 25/14; F04D 27/008; F04D 29/462; F16K 2099/0084; F16K 99/0032; F16K 99/0036; G01N 1/02; G01N 2001/027; G01N 2001/028; G01N 2035/00277; G01N 2035/00564; G01N 21/78; G01N 2458/30; G01N 27/28; G01N 27/327; G01N 27/3271; G01N 27/3272; G01N 27/3273; G01N 27/416; G01N 33/54306; G01N 33/54326; G01N 33/54333; G01N 33/54366; G01N 33/54373; G01N 33/5438; G01N 33/581; G01N 35/00029; G01N 35/0098; G01N 35/08; G01N 35/1095; G21C 1/324; G21C 15/24; G21C 15/253; H04M 1/72409; H04M 1/72412; Y02E 30/30; Y10S 224/918; Y10T 137/1797

See application file for complete search history.

(56) References Cited

U.S. PATENT DOCUMENTS

| 2009/0078253 | A1* | 3/2009 | Bao | A61M 16/208 |
| | | | | 128/203.26 |
| 2015/0122252 | A1* | 5/2015 | Frija | A24F 40/65 |
| | | | | 128/202.21 |
| 2018/0311156 | A1* | 11/2018 | Yadidi | A61M 15/0045 |
| 2021/0052014 | A1* | 2/2021 | Hejazi | A61M 11/04 |

FOREIGN PATENT DOCUMENTS

| WO | WO-2017032695 | A1 * | 3/2017 | ........... A24B 15/167 |
| WO | WO-2019126805 | A1 * | 6/2019 | ........... G05B 19/042 |
| WO | WO-2019130158 | A1 * | 7/2019 | ........... A24B 15/186 |

* cited by examiner

AUTHENTICATABLE INHALATION SYSTEM

CROSS-REFERENCE TO RELATED APPLICATIONS

This application claims priority to and the benefit of the provisional patent application titled "Valloons Vapor Filled Balloons Bio-Directional Combination Lock Inhaler with Identification Verification & Fingerprint Application", application No. 62/903,301, filed in the United States Patent and Trademark Office on Sep. 20, 2019. The specification of the above referenced patent application is incorporated herein by reference in its entirety.

BACKGROUND

Technical Field

The embodiments herein, in general, relate to inhalation systems. More particularly, the embodiments herein relate to an authenticatable inhalation system with a mouthpiece assembly that prevents unauthorized access to contents of the inhalation system.

Description of the Related Art

Vaporizers typically use a convection method for transferring heat to a vaporizable substance, for example, active substance-containing fluids, plant material, etc., for generating vapor for applications such as inhalation therapy, aromatherapy, etc. Some inhalation systems comprise a fluid container such as a balloon or a bag filled with vapor, which is attached to a mouthpiece to allow a user to inhale the vapor from the fluid container. To fill the balloon with inhalable vapor, the balloon is first attached to a flavor cartridge, then the flavor cartridge valve is attached to the nozzle of a crucible chamber of a vaporizer, where heat or hot air is passed through a vaporizable substance to produce the inhalable vapor. The inhalable vapor is then transferred into the balloon using a fan. The balloon filled with the inhalable vapor is then detached from the vaporizer and connected to a mouthpiece through which users may consume the inhalable vapor by inhalation from the balloon.

Since the legalization of cannabis has stormed the United States of America, which at the time of this writing, has currently two-thirds of the States having some form of legal legislation regarding the use of cannabis, many people may try cannabis for the first time, either medically or recreationally. Some desktop vaporizers provide for the containing of plant material such as cannabis flowers, and pass hot air through the cannabis flowers to release cannabinoids into the crucible chamber. Using a fan, the released cannabinoids are then transferred into a balloon attached to the nozzle of the crucible chamber. The balloon filled with the released cannabinoids is then detached from the nozzle and connected to a mouthpiece through which users may consume the released cannabinoids in the form of a vapor by inhalation from the balloon. Cannabis typically releases a foul odor into the ambient environment. Most people may find the foul odor of cannabis undesirable and may decline to have that odor inside of their homes. Moreover, some consumers may prefer not to consume raw cannabis vapor. Therefore, there is a need for combining a desirable flavor or aroma to cannabis and other inhaling substances.

Furthermore, when consumers use electronic vaporizers such as those used in electronic cigarettes (e-cigarettes), vape pens, etc., flavor is typically added using chemicals and artificial flavorings, or natural flavors from extracts or essential oils. However, when the temperature within the electronic vaporizers increases, for example, from between approximately 800 degrees Fahrenheit to about 1200 degrees Fahrenheit, the extreme heat generated releases toxins from the chemicals and artificial flavorings, or natural flavors from extracts or essential oils. These toxins, for example, carbon, carbon monoxide, carbon dioxide, formaldehyde, etc., are typically not harmful unless they are heated to a temperature whereby the toxins are released and tar begins to manifest and become consumed into the organs of a consumer's body, including the lungs.

Furthermore, some inhalation systems comprise complex structures therewithin for releasing vapors produced by a vaporizer into a balloon attached to the vaporizer. These complex structures take up a lot of space within the inhalation systems and increase the size and dimensions of the inhalation systems. Furthermore, conventional inhalation systems typically do not provide adequate protection for children and unauthorized users of pharmaceutical drugs or other recreational drugs administered through them. There is a need for authenticating users and inhalation systems prior to their use for preventing unauthorized access to contents of these inhalation systems. Moreover, there is a need for providing locking mechanisms in the inhalation systems that allow only authenticated users to access the contents of these inhalation systems.

Hence, there is a long-felt need for a compact inhalation system and a method for addressing the above-recited problems associated with the related art.

SUMMARY

This summary is provided to introduce a selection of concepts in a simplified form that are further disclosed in the detailed description. This summary is not intended to determine the scope of the claimed subject matter.

The compact inhalation system and the method disclosed herein address the above-recited need for combining a desirable flavor or aroma to an inhaling substance; authenticating users and the inhalation system prior to use thereof to prevent unauthorized access to contents of the inhalation system; providing locking mechanisms in the inhalation system that allow only authenticated users to access the contents of the inhalation system; and optimizing space within the inhalation system. Furthermore, the inhalation system and the method disclosed herein address the above-recited need for heating the inhaling substance to a temperature lower than a combustible temperature of the inhaling substance, thereby releasing only an inhaling fluid or aroma and not toxins present in the inhaling substance.

The inhalation system disclosed herein comprises a fluid transfer member, a valve member, a flavoring cartridge assembly, and a mouthpiece. In an embodiment, the fluid transfer member is an inflatable container, for example, a balloon or a bag, configured to inflate and contain an inhaling fluid received from the flavoring cartridge assembly in communication with a vaporizer. The fluid transfer member comprises an open end configured to receive the inhaling fluid. The inhaling fluid is, for example, a medicinal fluid, etc. The valve member is operably connected to the open end of the fluid transfer member. The valve member comprises a body, a first opening, and a second opening. The first opening of the valve member is configured to be connected to the open end of the fluid transfer member. The second opening of the valve member is configured to be connected to the mouthpiece and the vaporizer. In an embodiment, the inhalation system further comprises a locking member configured to lock the fluid transfer member to the valve member. The locking member comprises a lock opening for inserting the open end of the fluid transfer member. The locking member engageably connects the open end of the fluid transfer member to the first opening of the valve member.

The flavoring cartridge assembly is positioned within the body of the valve member. The flavoring cartridge assembly comprises a substance holder made of plastic, an absorbent member such as cotton, a guillotine method by which to automatically puncture to open the fluid substance holder member to release fluid into the absorbent member, a cylindrical stem which protrudes through the entire assembly, and a cartridge. The substance holder contains an inhaling substance, for example, a medicinal substance, a flavoring substance, etc., or a combination thereof. The absorbent member, for example, a pad made of a cotton material or another absorbent material, is positioned proximal to the substance holder. The absorbent member is configured to absorb the inhaling substance received from the substance holder. The cartridge accommodates the substance holder and the absorbent member. In an embodiment, the absorbent member is positioned below the substance holder in the cartridge. There is also a guillotine styled member with sharp pointed pins protruding downwards towards the substance holder which is suspended over top of the substance holder member. When the consumer first engages with the flavoring cartridge valve, the action of unscrewing the stem from the valve causes the guillotine member with pins to puncture the substance holder member to release the substance into the absorbent member. When the guillotine member punctures the plastic substance holder member, the sharp pointed pins remain descended into the substance holder member to create a plug which prevents too much of the substance member to leak out into the absorbent member at once. Similar to a car's tire that is plugged with a nail, the air leaks slowly from the tire. But if the nail is removed, the air all leaks out at once. In a similar fashion, the guillotine member's pins are further used to cause a slow leak of the substance by causing the pins to remain lodged into the plastic substance holder member, to provide for multiple sessions of usage by the consumer over several days. When the second opening of the valve member is connected to the vaporizer, the vaporizer heats the absorbent member with the absorbed inhaling substance to a temperature lower than a combustible temperature of the inhaling substance for vaporizing the inhaling substance and releasing the inhaling fluid once converted to vapor by the heat from the vaporizer into the fluid transfer member. In an embodiment, the cartridge comprises one or more inlet ports and multiple outlet ports. The inlet ports are positioned on an outer periphery of the cartridge. The outlet ports are positioned on an inner periphery of the cartridge for releasing the inhaling fluid once converted to vapor by the heat from the vaporizer. In an embodiment, the fluid transfer member inflates and contains the inhaling fluid received from the cartridge of the cartridge assembly in communication with the vaporizer.

In an embodiment, the inhaling substance comprises a flavoring substance. In an embodiment, the flavoring substance comprises one or more flavors selected from a group comprising a fruit flavor and a secondary flavor. When the second opening of the valve member is connected to the vaporizer, the vaporizer heats the absorbent member containing the flavoring substance accommodated in the cartridge to a temperature lower than a combustible temperature of the flavoring substance for vaporizing the flavoring substance and converting it to vapor by the heat from the vaporizer, releasing a flavored aroma vapor from the absorbent member into the fluid transfer member. The fluid transfer member receives and contains the flavored fluid vapor therewithin.

In an embodiment, the substance holder is configured as a ring-shaped member and the cartridge is configured as ring-shaped members comprising central openings. In this embodiment, the cartridge assembly comprises a stem member, a guillotine-styled cap with pins member, and a collapsible spring member. The stem member is configured to coaxially accommodate the cartridge with the substance holder through the central openings of the cartridge and the substance holder. The stem member comprises an upper end and a lower end. The upper end of the stem member is connected to the open end of the fluid transfer member. In an embodiment, the stem member is twistably removed from the body of the valve member prior to connecting the second opening of the valve member to the vaporizer. In an embodiment, the lower end of the stem member is configured to be connected to the mouthpiece and the vaporizer. In an embodiment, the lower end of the stem member is configured as a non-locking mouthpiece. The cap member is coaxially positioned on the stem member through a central opening of the cap member. The guillotine-styled cap with pins member is suspended above the substance holder. In an embodiment, the cap member comprises pins extending downwardly from a lower surface of the cap member. The pins of the cap member are configured to puncture the substance holder and release the inhaling substance into the absorbent member accommodated in the cartridge. In an embodiment, the pins of the cap member are also configured to plug the substance holder after puncturing the substance holder. The collapsible spring member is coaxially positioned on the stem member through a central opening of the collapsible spring member and positioned above the cap member. The collapsible spring member is configured to push the cap member with the pins downwards towards the substance holder for puncturing the substance holder and releasing the inhaling substance into the absorbent member accommodated in the cartridge. The collapsible spring member is configured to create a funnel for harnessing the inhaling fluid into the fluid transfer member and preventing waste from dissipating while passing through the cartridge assembly. In an embodiment, the collapsible spring member is configured to collapse into a flat structure during compression to optimize space within the valve member.

When the second opening of the valve member is disconnected from the vaporizer and operably connected to the mouthpiece, the valve member transfers the inhaling fluid or the flavored fluid converted to vapor during the heating process by the vaporizer, flowing from the fluid transfer member to a mouth of a user via the mouthpiece. In an embodiment, the valve member is configured as a non-locking mouthpiece. In an embodiment, the fluid transfer member is a hose member comprising an open first end and an open second end. In this embodiment, the open first end of the hose member is operably connected to the first opening of the valve member, while the second opening of the valve member remains connected to the vaporizer. Moreover, in this embodiment, the open second end of the hose member, that is distal to the open first end of the hose member, is operably connected to the mouthpiece. The hose member is configured to transfer the inhaling fluid or the flavored fluid received from the cartridge assembly in communication with the vaporizer to the user's mouth via the mouthpiece.

In another embodiment, the valve member is configured as a locking mouthpiece assembly. The locking mouthpiece assembly is configured to allow authentication of the user prior to releasing the inhaling fluid to the user's mouth via the mouthpiece. In an embodiment, the valve member configured as a locking mouthpiece assembly comprises an enclosure, a first flywheel, a stabilization pin, a second flywheel, a cylindrical member, and the mouthpiece. The enclosure comprises a first end and a second end. The first flywheel is built into the first end of the enclosure. The first flywheel comprises passageways in fluid communication with the first opening of the valve member for allowing flow of the inhaling fluid from the fluid transfer member into the enclosure and out to the mouthpiece. The stabilization pin is attached to the first flywheel and positioned within the enclosure. The stabilization pin extends from the first flywheel to a tip of the mouthpiece. The stabilization pin is configured with an inscribing scroll for inscribing a randomly generated bidirectional path and one or more identification elements thereon. The identification elements, for example, barcodes, serial numbers, etc., are configured to identify the inhalation system. In an embodiment, the identification elements are configured to be input into a mobile application deployed on a user device. The mobile application is in operable communication with an authentication server via a network for identifying the inhalation system and authenticating the user. In an embodiment, the authentication server stores identification information of the inhalation system and the user.

The second flywheel and the cylindrical member are positioned coaxially around the stabilization pin. The second flywheel and the cylindrical member operably communicate with each other for opening and closing the passageways of the first flywheel and controlling access to the inhaling fluid in the fluid transfer member. The cylindrical member comprises track pins configured to navigate through the bidirectional path along the inscribing scroll to unlock the valve member. In an embodiment, a display area is positioned on the stabilization pin for displaying authentication elements, for example, combination lock letters and numerals, along an X-axis and a Y-axis. In an embodiment, the enclosure of the mouthpiece assembly comprises a window configured to allow viewing of the authentication elements inscribed on the stabilization pin.

The mouthpiece is operably connected to the second end of the enclosure. In an embodiment, the mouthpiece is positioned proximal to the display area. The mouthpiece is configured to receive and transfer the inhaling fluid flowing from the enclosure to the user's mouth. In an embodiment, the inhalation system further comprises tab elements positioned on one end of the second flywheel and on one end of the cylindrical member. The tab elements of the second flywheel and the cylindrical member are in operable communication for opening and closing the passageways of the first flywheel. In another embodiment, the inhalation system further comprises tab elements positioned on the cylindrical member for precluding the cylindrical member from moving a substantial distance around the stabilization pin within the enclosure.

Disclosed herein is also a method for providing and using an inhalation system with user authentication. In the method disclosed herein, the inhalation system comprising the fluid transfer member, the valve member configured as a locking mouthpiece assembly, and the cartridge assembly as disclosed above is assembled. Furthermore, in the method disclosed herein, a user connects the first opening of the valve member to an open end of the fluid transfer member, for example, an inflatable container such as a balloon, and connects the second opening of the valve member to the vaporizer. The vaporizer generates and transfers heat to the cartridge assembly positioned within the body of the valve member. The generated and transferred heat heats the absorbent member with the inhaling substance received from the substance holder to a temperature lower than a combustible temperature of the inhaling substance. On receiving the heat from the vaporizer, the inhaling substance in the absorbent member of the cartridge assembly is vaporized. The cartridge assembly releases an inhaling fluid to the fluid transfer member via the first opening of the valve member. The fluid transfer member receives and contains the inhaling fluid therewithin. The user then disconnects the second opening of the valve member from the vaporizer and connects the second opening of the valve member to the mouthpiece.

In an embodiment, the authentication of the user comprises communicating one or more identification elements of the inhalation system and user information by the mobile application to the authentication server via a network. The user information comprises, for example, one or more of an identification element of the user, an image of the user along with the identification element of the user, and biometric information of the user. The authentication server is configured to verify identification information of the user by executing a facial recognition technique on the image and the identification element. On successful verification of the identification elements of the inhalation system and the user information, the mobile application receives an authentication code comprising a predefined combination of authentication elements associated with the inhalation system from the authentication server via the network for navigating the randomly generated bidirectional path and unlocking the valve member.

In an embodiment, the user is authenticated using the valve member configured as the locking mouthpiece assembly, the mobile application deployed on a user device, and the authentication server as follows: The mobile application requests the user to enter or scan identification elements, for example, barcodes, serial numbers, etc., inscribed on the inhalation system. When the user enters or scans the identification elements of the inhalation system into the mobile application on the user device, the mobile application communicates the identification elements to the authentication server via a network, for example, the internet. The mobile application then requests the user to scan an identification element of the user, for example, a driver's license of the user. When the user scans the user's identification element into the mobile application, the mobile application communicates the identification element to the authentication server via the network. The mobile application then requests the user to capture the user's image along with the user's identification element. When the user captures the image along with the user's identification element, the mobile application communicates the user's image along with the identification element of the user to the authentication server via the network. In an embodiment, the authentication server verifies identification information of the user by executing a facial recognition technique on the image and the identification element. The mobile application then requests the user to input the user's biometric information, for example, a fingerprint. When the user inputs the biometric information into the mobile application, the mobile application communicates the biometric information to the authentication server via the network. On successful verification of the identification elements of the inhalation system, the identification information of the user, and the biometric information of the user by the authentication server, the mobile application receives an authentication code comprising a predefined combination of the authentication elements associated with the inhalation system from the authentication server via the network for navigating the randomly generated bidirectional path and unlocking the valve member. The window in the enclosure of the valve member allows the user to view the authentication elements inscribed on the stabilization pin. The user unlocks the valve member by using the authentication code and navigating the randomly generated bidirectional path configured in the valve member. The unlocked, valve member then transfers the inhaling fluid from the fluid transfer member to the user's mouth via the mouthpiece.

In one or more embodiments, related systems comprise circuitry and/or programming for executing the methods disclosed herein. The circuitry and/or programming are of any combination of hardware, software, and/or firmware configured to execute the methods disclosed herein depending upon the design choices of a system designer. In an embodiment, various structural elements are employed depending on the design choices of the system designer.

BRIEF DESCRIPTION OF THE DRAWINGS

The foregoing summary, as well as the following detailed description, is better understood when read in conjunction with the appended drawings. For illustrating the embodiments herein, exemplary constructions of the embodiments are shown in the drawings. However, the embodiments herein are not limited to the specific structures, components, and methods disclosed herein. The description of a structure or a component or a method step referenced by a numeral in a drawing is applicable to the description of that structure or component or method step shown by that same numeral in any subsequent drawing herein.

DETAILED DESCRIPTION

Figure 1:
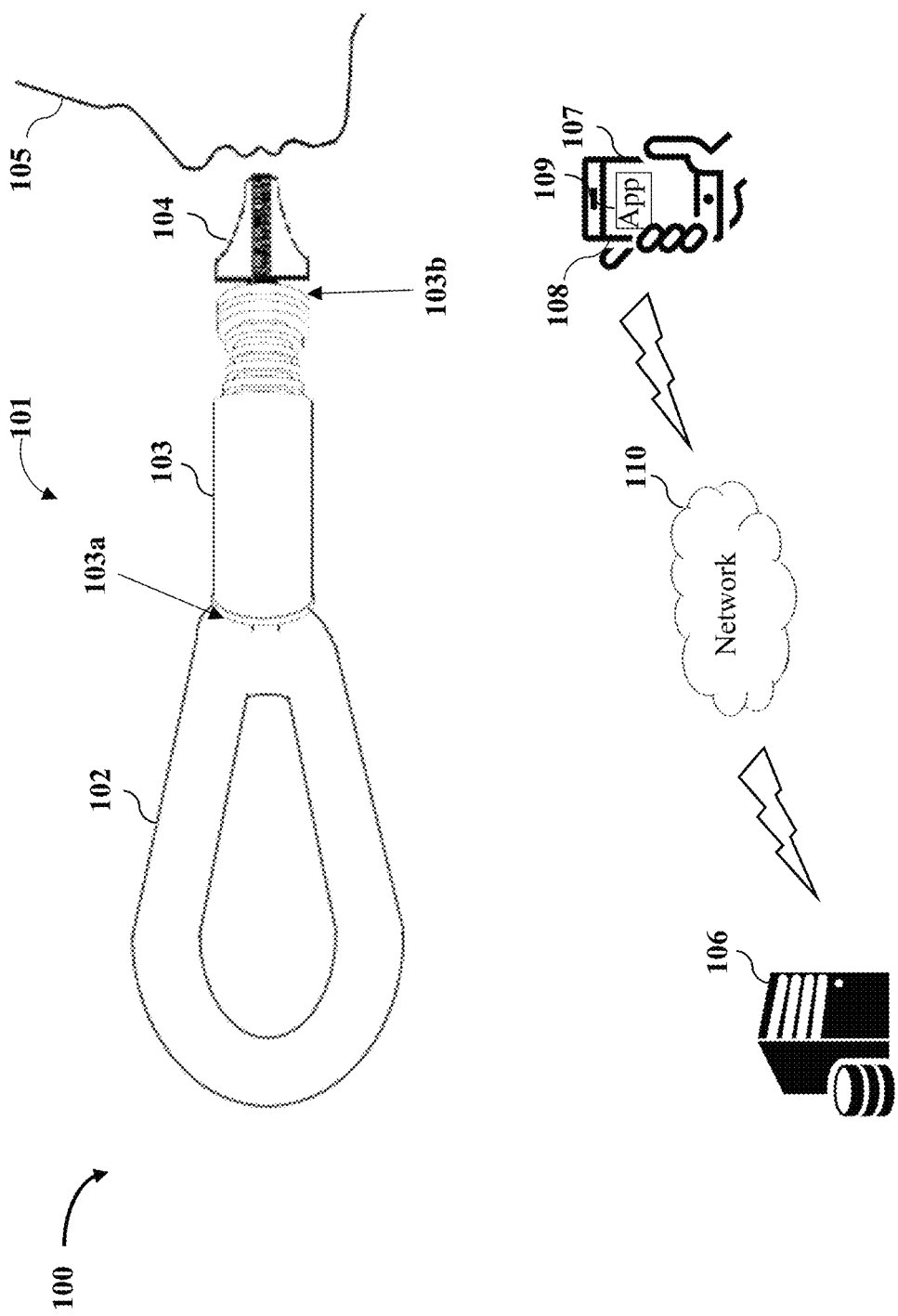
FIG. 1 illustrates a system comprising an authenticatable inhalation system, a mobile application deployed on a user device, and an authentication server, according to an embodiment herein.
Figure 2:
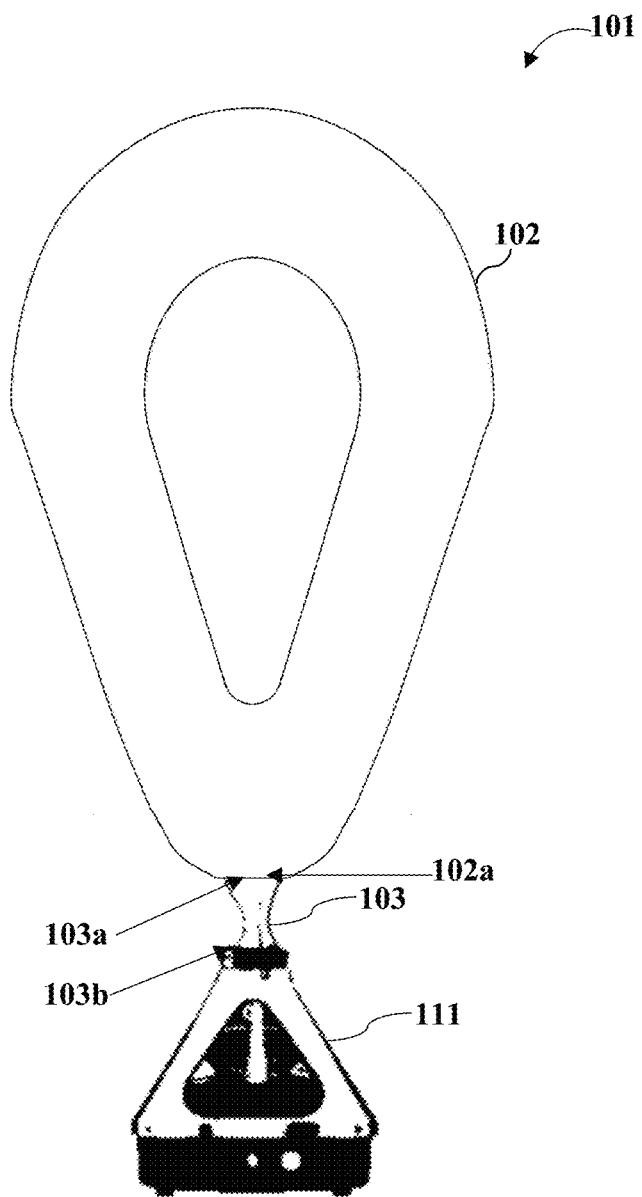
FIG. 2 illustrates a front view showing a fluid transfer member configured as an inflatable container and connected to a vaporizer via a valve member of the inhalation system, according to an embodiment herein.

FIG. 1 illustrates a system 100 comprising an authenticatable inhalation system 101, a mobile application 109 deployed on a user device 107, and an authentication server 106, according to an embodiment herein. In an embodiment, the authenticatable inhalation system 101 disclosed herein comprises a fluid transfer member configured to contain an inhaling fluid, for example, a gas, a liquid, a vapor, an aroma, etc. The inhaling fluid is, for example, a medicinal fluid, etc. In an embodiment, the fluid transfer member is configured as an inflatable container 102, for example, a balloon or a bag. In an embodiment, the inflatable container 102 is a hollow teardrop shaped balloon as illustrated in FIG. 1. In another embodiment, the fluid transfer member is a hose member 127 comprising an open first end 127a and an open second end 127b as illustrated in FIG. 10. In this embodiment, the open first end 127a of the hose member 127 is operably connected to the first opening 103a of the valve member 103, while the second opening 103b of the valve member 103 is connected to a vaporizer 111 as illustrated in FIG. 2. Moreover, in this embodiment, the open second end 127b of the hose member 127, that is distal to the open first end 127a of the hose member 127, is operably connected to a mouthpiece 104. For purposes of illustration, the detailed description refers to the fluid transfer member being an inflatable container 102 as illustrated in FIGS. 1-2, FIG. 4, and FIGS. 9C-9G; however the scope of the system 100 and the method disclosed herein is not limited to the fluid transfer member being an inflatable container 102 but may be extended to include any type of fluid transfer member, for example, a hose member 127 as illustrated in FIG. 10 or other functionally equivalent structures.

The authenticatable inhalation system 101 disclosed herein further comprises a valve member 103 and a mouthpiece 104. The valve member 103 is operably connected to the fluid transfer member. The valve member 103 comprising a first opening 103a and a second opening 103b. The first opening 103a of the valve member 103 is connected to the fluid transfer member. To first fill the fluid transfer member with the inhaling fluid, the second opening 103b of the valve member 103 is connected to a vaporizer 111. In an embodiment, the valve member 103 is configured as a non-locking mouthpiece. In another embodiment, the valve member 103 is configured as a locking mouthpiece assembly as illustrated in FIG. 1. After the fluid transfer member is filled with the inhaling fluid using the vaporizer 111, the second opening 103b of the valve member 103 is disconnected from the vaporizer 111 and connected to the mouthpiece 104 as illustrated in FIG. 1. The inhaling fluid is extracted from the fluid transfer member through the mouthpiece 104 and inhaled by a user 105.

In an embodiment, the authenticatable inhalation system 101 comprises one or more identification elements, for example, barcodes, serial numbers, etc., inscribed on the mouthpiece 104 as illustrated in FIG. 1. In an embodiment, the mobile application 109 renders a display interface 108 for scanning the identification elements positioned on the authenticatable inhalation system 101. The user 105 scans the identification elements using the mobile application 109 on the user device 107. The user device 107 is an electronic device, for example, a smart phone, a tablet computing device, a mobile computer, a mobile phone, a personal digital assistant, a wearable computing device such as smart glasses, a smart watch, etc., a touch centric device, etc. The mobile application 109 is in operable communication with the authentication server 106 via a network 110 for identifying the inhalation system 101 and authenticating the user 105. The network 110 is, for example, one of the internet, an intranet, a wired network, a wireless network, a communication network that implements Bluetooth® of Bluetooth Sig, Inc., a network that implements Wi-Fi® of Wi-Fi Alliance Corporation, an ultra-wideband (UWB) communication network, a wireless universal serial bus (USB) communication network, a communication network that implements ZigBee® of ZigBee Alliance Corporation, a general packet radio service (GPRS) network, a mobile telecommunication network such as a global system for mobile (GSM) communications network, a code division multiple access (CDMA) network, a third generation (3G) mobile communication network, a fourth generation (4G) mobile communication network, a fifth generation (5G) mobile communication network, a long-term evolution (LTE) mobile communication network, a public telephone network, etc., a local area network, a wide area network, an internet connection network, an infrared communication network, etc., or a network formed from any combination of these networks. In an embodiment, the authentication server 106 stores identification information of the inhalation system 101 and identification information, for example, user details, fingerprints, etc., of the user 105. The mobile application 109 receives and transmits the scanned identification elements of the authenticatable inhalation system 101 to the authentication server 106 via the network 110. The mobile application 109 communicates with the authentication server 106 to perform additional levels of authentication and verification of the inhalation system 101 and the user's 105 identity as disclosed in the detailed description of FIG. 12.

FIG. 2 illustrates a front view showing a fluid transfer member configured, for example, as an inflatable container 102 and connected to a vaporizer 111 via the valve member 103 of the inhalation system 101, according to an embodiment herein. In an embodiment, the inflatable container 102 is configured in a V-shape with a crescent overtop for providing circulation of an inhaling fluid inside the inflatable container 102 in a continuous circular motion to prevent the inhaling fluid from becoming stale and/or sticking to the inside of the inflatable container 102 before the inhaling fluid is consumed. The inflatable container 102 comprises an open end 102a configured to receive an inhaling fluid. The inflatable container 102 is configured to contain the received inhaling fluid therewithin. The first opening 103a of the valve member 103 is operably connected to the open end 102a of the inflatable container 102. The second opening 103b of the valve member 103 is operably connected to the vaporizer 111. In an embodiment, the vaporizer 111 comprises a hot air generator (not shown) that draws air from an air inlet positioned on a lower surface of the vaporizer 111, heats the drawn air, and transfers the heated air in an upward direction in the vaporizer 111. In an embodiment, the vaporizer 111 comprises a chamber that accommodates a vaporizing substance, for example, a plant material. The heated air is transferred to the vaporizing substance to produce an inhaling fluid. The inhaling fluid is transferred by a fan (not shown) in the vaporizer 111 to the inflatable container 102 via the valve member 103.

Figure 3A:
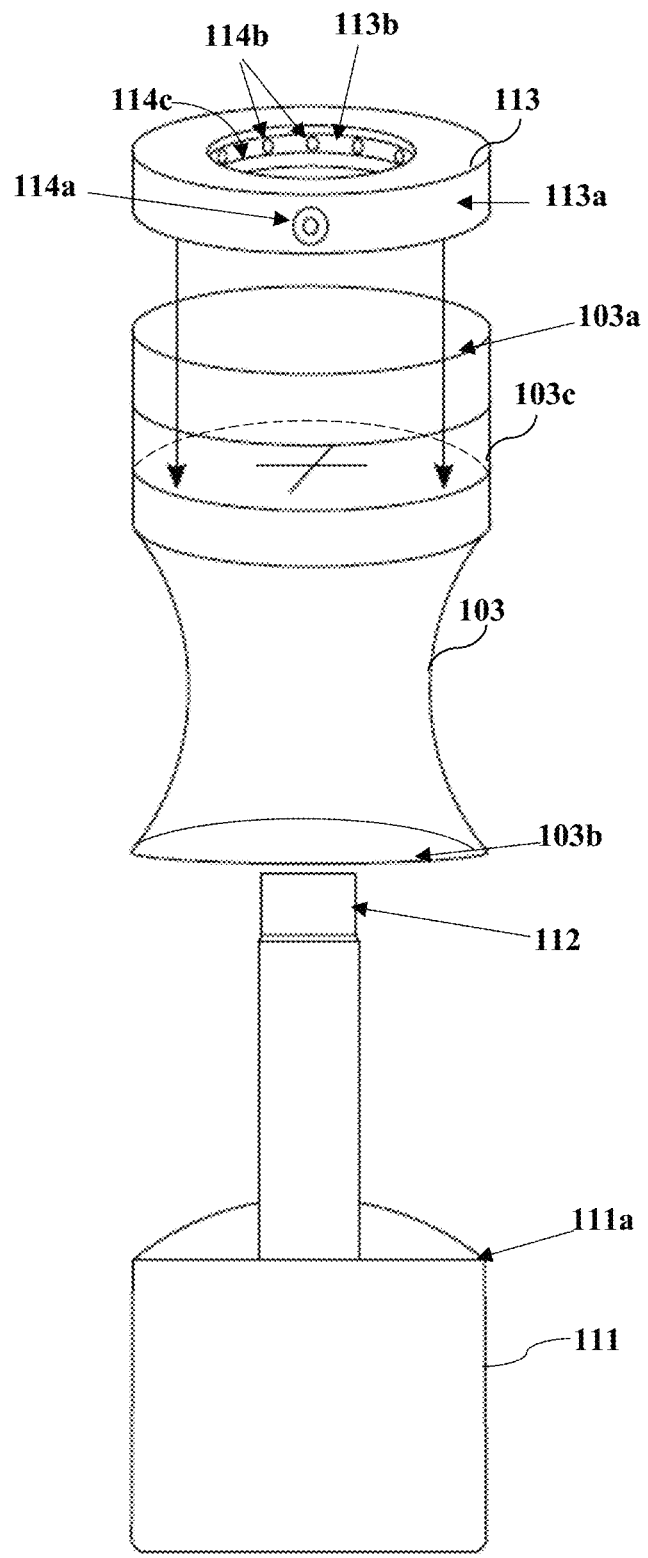
FIGS. 3A-3B illustrates front views showing positioning of a cartridge within a body of the valve member and positioning of the valve member onto a nozzle of the vaporizer of the inhalation system, according to an embodiment herein.
Figure 3B:
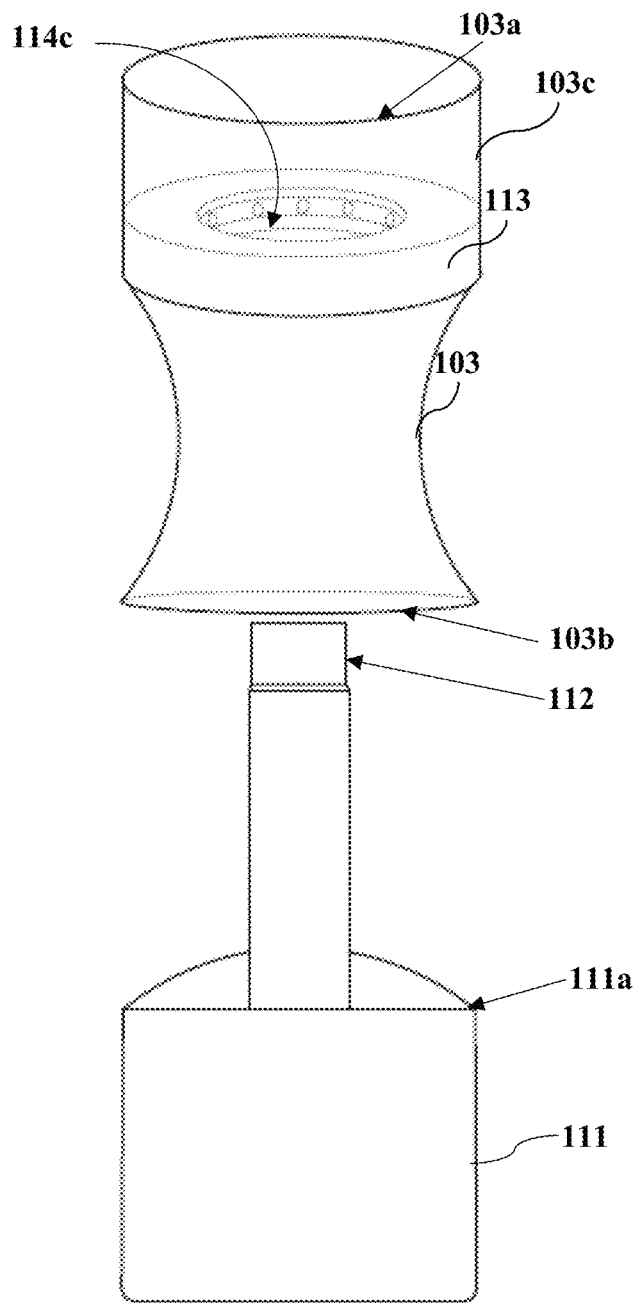

FIGS. 3A-3B illustrate front views showing positioning of a cartridge 113 within a body 103c of the valve member 103 and positioning of the valve member 103 onto a nozzle 112 of the vaporizer 111 of the inhalation system 101 shown in FIG. 1, according to an embodiment herein. As illustrated in FIG. 3A, the valve member 103 further comprises a body 103c defined between the first opening 103a and the second opening 103b. In an embodiment, in addition to the fluid transfer member, the valve member 103, and the mouthpiece 104 illustrated in FIG. 1, the inhalation system 101 further comprises a cartridge 113 configured to accommodate a substance holder and an absorbent member. The substance holder contains an inhaling substance, for example, a medicinal substance, a psychoactive substance, an essential oil that is safe for human consumption, ingestion or inhalation, a flavoring substance, etc., or a combination thereof. The absorbent member, for example, a pad made of a cotton material or another absorbent material, is positioned proximal to the substance holder. The absorbent member is configured to absorb the inhaling substance received from the substance holder. In an embodiment, the absorbent member is positioned below the substance holder in the cartridge 113. In an embodiment, the cartridge 113 comprises one or more inlet ports 114a, multiple outlet ports 114b, and a central opening 114c. For example, an inlet port 114a is positioned on an outer periphery 113a of the cartridge 113 for inserting the absorbent member as illustrated in FIG. 3A. The outlet ports 114b are positioned on an inner periphery 113b of the cartridge 113 for releasing the inhaling fluid.

In an embodiment, the inhaling substance comprises a flavoring substance. Heating of the flavoring substance produces a flavored fluid that flavors the inhaling fluid produced from a vaporizing substance accommodated in the chamber of the vaporizer 111 shown in FIG. 2. The flavoring substance comprises one or more flavors selected from a group comprising a fruit flavor and a secondary flavor. The flavors comprise, for example, watermelon, strawberry, chocolate, banana, caramel, peach, mango, cherry, apple, etc., flavors and any combination thereof. In an embodiment, the flavoring substance is administered in the form of drops to the absorbent member. The flavoring substance is used to flavor the inhaling fluid, for example, a plant matter vapor inside the vaporizer 111 to provide a desirable aroma to the odor of the plant matter. The absorbent member is then inserted into the cartridge 113 through the inlet port 114a.

The cartridge 113 is positioned within the body 103c of the valve member 103 as illustrated in FIG. 3B. The second opening 103b of the valve member 103 is configured to be connected to an upper section 111a of the vaporizer 111 as illustrated in FIG. 3B, and to a mouthpiece 104 as illustrated in FIG. 1. The vaporizer 111 comprises an elongate nozzle 112 configured to be inserted through the valve member 103 and the central opening 114c of the cartridge 113. The second opening 103b of the valve member 103 fits over the elongate nozzle 112 of the vaporizer 111 to allow heat from the vaporizer 111 to flow through the valve member 103 to cause the cartridge 113 to aromatize the flavor contained in the cartridge 113 and transfer the flavor to the fluid transfer member, for example, the inflatable container 102 illustrated in FIG. 2. When the second opening 103b of the valve member 103 is connected to the vaporizer 111, the vaporizer 111 is configured to heat the absorbent member with the absorbed flavoring substance accommodated in the cartridge 113 to a temperature lower than a combustible temperature of the flavoring substance for vaporizing the flavoring substance and releasing a flavored fluid from the absorbent member into the fluid transfer member. In an example, if the vaporizer 111 produces a cannabis vapor, the flavored fluid flavors the cannabis vapor with fruit flavors during the vaporization process, while releasing pleasant aromas into the ambient atmosphere. The inhalation system 101 creates an illusion to the user who is consuming the flavored fluid or the aroma through the nostrils or the back of the throat which makes the user believe they are tasting the flavor, when they are actually smelling the flavor. The flavored fluid also helps to cover over the smell or odor of plant material, thereby providing a pleasant aroma in the ambient atmosphere.

Figure 4:
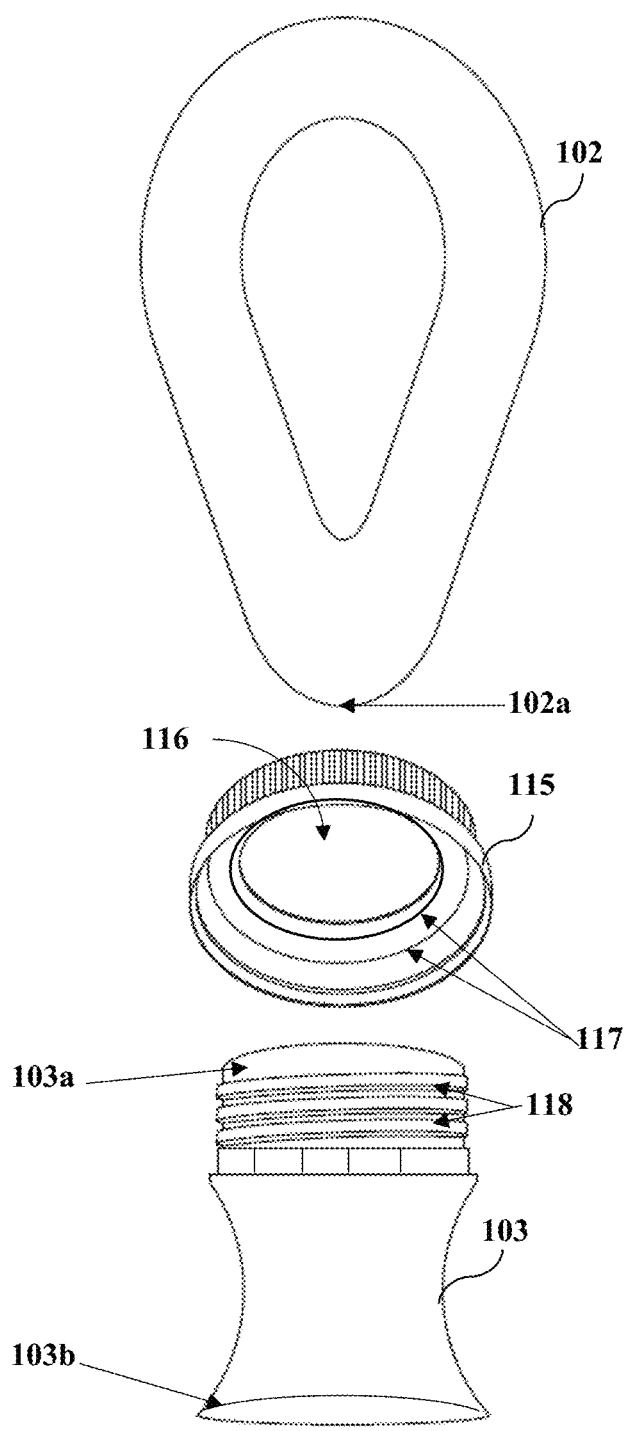
FIG. 4 illustrates a partial exploded view of the inhalation system, showing a locking member for locking the fluid transfer member to the valve member, according to an embodiment herein.

FIG. 4 illustrates a partial exploded view of the inhalation system 101 shown in FIG. 1, showing a locking member 115 for locking the fluid transfer member configured, for example, as an inflatable container 102, to the valve member 103, according to an embodiment herein. In an embodiment, the inhalation system 101 further comprises a locking member 115 configured to lock the inflatable container 102 to the valve member 103. The locking member 115 comprises a lock opening 116 for inserting the open end 102a of the inflatable container 102. The locking member 115 is configured to engageably connect the open end 102a of the inflatable container 102 to the first opening 103a of the valve member 103. In an embodiment, the valve member 103 comprises screw threads 118 configured proximal to the first opening 103a of the valve member 103. The locking member 115 comprises internal threads 117 configured to engage with the screw threads 118 of the valve member 103 and firmly lock the inflatable container 102 to the valve member 103. The open end 102a of the inflatable container 102 is inserted through the lock opening 116 of the locking member 115. The locking member 115 is then positioned on the first opening 103a of the valve member 103 and screwed or ratcheted into position until the locking member 115 is firmly locked to the valve member 103. The locking member 115 prevents unauthorized access to the inflatable container 102 containing the inhaling fluid. The locking member 115 also creates an airtight valve member 103 for securing the cartridge 113 illustrated in FIGS. 3A-3B, and preventing the inhaling substance and/or the flavoring substance from drying out. Once the locking member 115 securely locks the inflatable container 102 to the valve member 103, the inflatable container 102 cannot be unlocked.

Figure 5A:
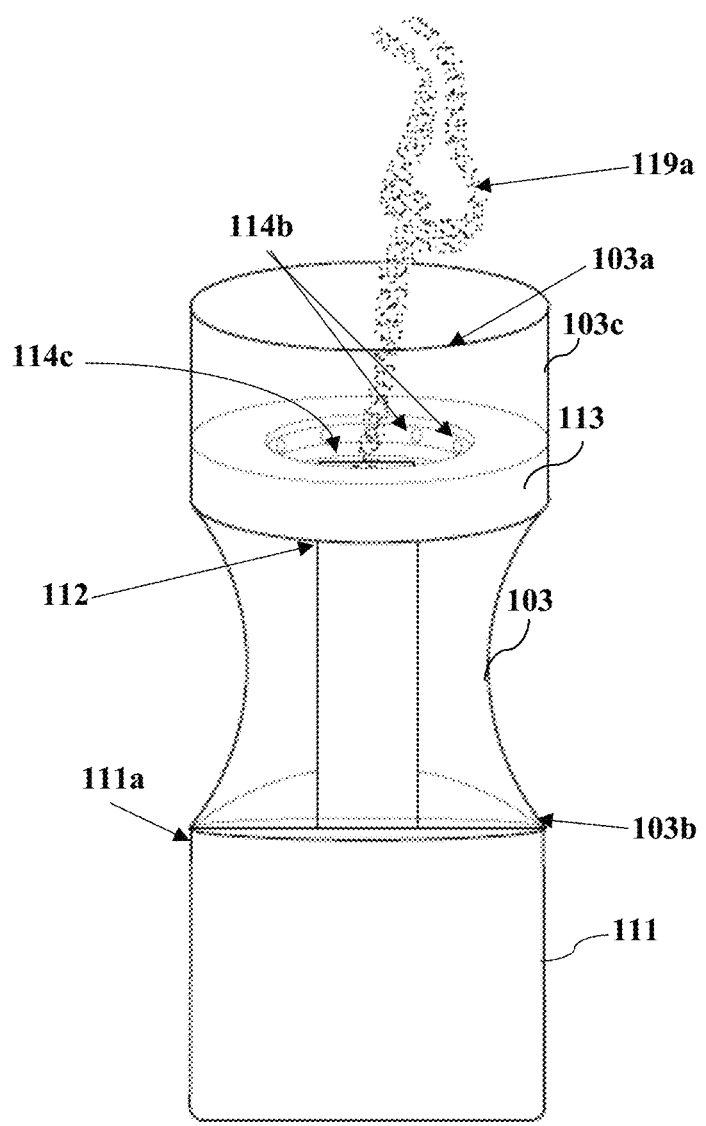
FIGS. 5A-5B illustrates front views showing generation of a flavored inhaling fluid from the cartridge in communication with the vaporizer of the inhalation system, according to an embodiment herein.
Figure 5B:
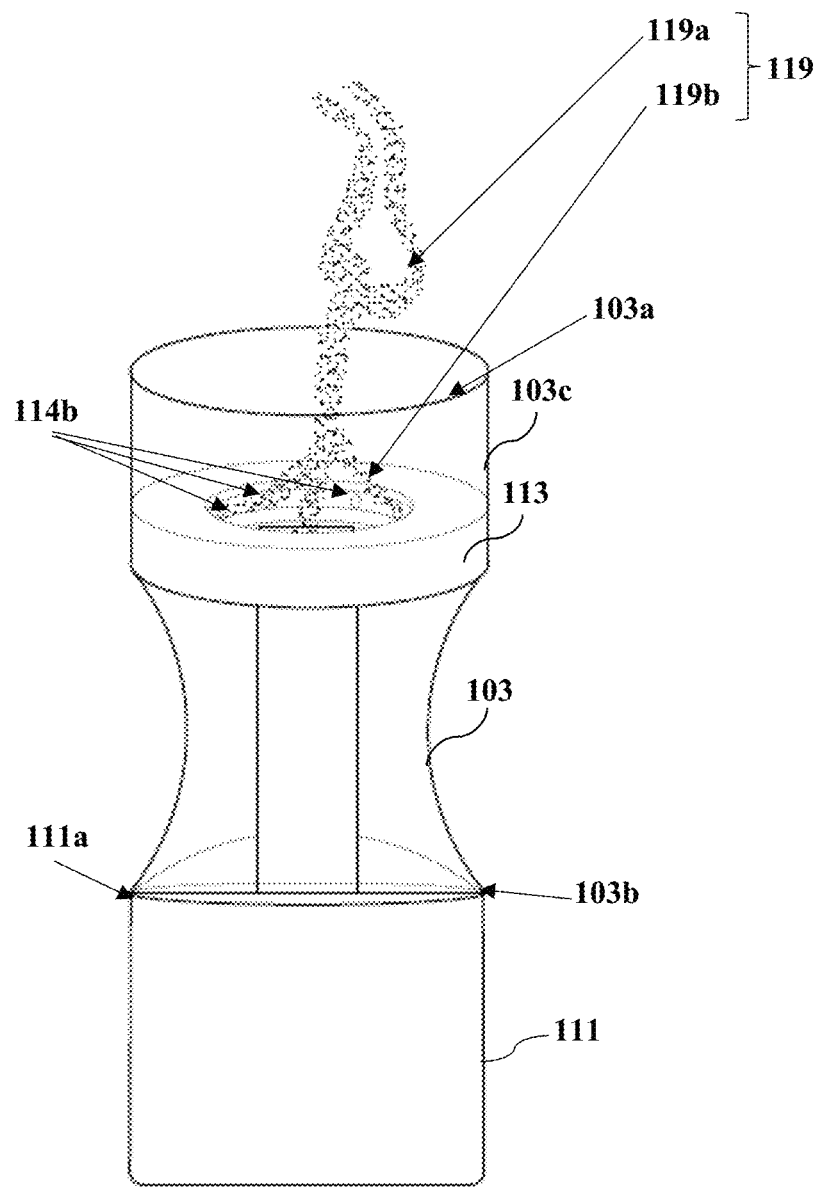

FIGS. 5A-5B illustrate front views showing generation of a flavored inhaling fluid 119 from the cartridge 113 in communication with the vaporizer 111 of the inhalation system 101 shown in FIG. 1, according to an embodiment herein. The cartridge 113 configured as a flavor disc is positioned within the body 103c of the valve member 103. The valve member 103 is positioned on the upper section 111a of the vaporizer 111 such that the nozzle 112 is inserted through the central opening 114c of the cartridge 113. The fluid transfer member, for example, the inflatable container 102, is then locked to the valve member 103 using the locking member 115 illustrated in FIG. 4. The cartridge 113 lies between the nozzle 112 of the vaporizer 111 and the open end 102a of the inflatable container 102. The vaporizer 111 is activated to initiate heat generation to fill the inflatable container 102 with a flavored inhaling fluid 119. The heat that rises through the valve member 103 from the vaporizer 111 increases the temperature of the cartridge 113 to the temperature required to initiate vaporization of the flavoring substance contained in the substance holder and released into the absorbent member in the cartridge 113. In an embodiment, the heat that rises through the valve member 103 from the vaporizer 111 heats the cartridge 113 to a temperature lower than a combustible temperature of the flavoring substance to initiate vaporization of the flavoring substance contained in the substance holder and released into the absorbent member in the cartridge 113. Heating the flavoring substance to a temperature lower than that of the combustible temperature of the flavoring substance causing only the aroma or flavor to be emitted and not the toxins present in the flavoring substance. The inhalation system 101 therefore operates not only in the vaporizer 111, but also uses a portion of the heat dissipated from the vaporizer 111 to gently heat the flavoring substance. Although the direct heat inside the vaporizer 111 may rise, for example, from about 350 degrees Fahrenheit to about 400 degrees Fahrenheit, this heat quickly dissipates after leaving the crucible chamber of the vaporizer 111. The cartridge 113 containing the flavoring substance is positioned outside of the crucible chamber and the vaporizer 111 and begins to heat the flavoring substance using the dissipated heat, which warms the flavoring substance from its normal temperature, that is, below room temperature. During the time that the flavored fluid 119b takes to completely fill the inflatable container 102, the dissipated heat from the vaporizer 111 reaches the cartridge 113 and begins to heat the flavoring substance from scratch to a temperature below its flash point, which is warm enough to gently emit a flavored fluid 119b or aroma from the flavoring substance. This emission of the aroma is sensed by smell receptors and travels to a user's brain. The brain is then confused by the sense of smell and equates the sense of smell to its sense of taste. The user then experiences an illusion of the inhaling fluid having flavor, and the vaporized material or fluid 119a from the vaporizer 111 is given a mask of the aroma from the flavored fluid 119b, thereby adding a different or a better aroma to the ambient atmosphere, while simultaneously causing the illusion of flavor to the user.

The heat from the vaporizer 111 enters the cartridge 113 through the outlet ports 114b of the cartridge 113. The flavoring substance vaporizes and moves into the inflatable container 102 through a force of a fan (not shown) positioned in the vaporizer 111. Once heated, the cartridge 113 releases the vaporized flavoring substance in the form of a flavored fluid 119b through the outlet ports 114b to the inflatable container 102, or in an embodiment, to the ambient atmosphere. The flavored fluid 119b combines with the inhaling fluid 119a, for example, a medicinal vapor or a cannabis vapor received from the chamber of the vaporizer 111 into the inflatable container 102. The inflatable container 102 receives and contains the flavored inhaling fluid 119. The inflatable container 102 inflates on receiving the flavored inhaling fluid 119. The inflatable container 102 contains the received flavored inhaling fluid 119 therewithin. The valve member 103 with the inflatable container 102 is then disconnected from the vaporizer 111 and connected to the mouthpiece illustrated in FIG. 1. That is, after the inflatable container 102 is filled with the flavored inhaling fluid 119 that has passed through the valve member 103 connected to the elongate nozzle 112 of the vaporizer 111, the valve member 103 is removed from the vaporizer 111. The mouthpiece 104 is inserted through the second opening 103b of the valve member 103 as illustrated in FIG. 9F, that previously connected to the elongate nozzle 112 of the vaporizer 111. Through a series of twists, turns, pushes, and pulls of the mouthpiece 104 shown in FIG. 1, an air passageway is opened to allow access to the flavored inhaling fluid 119 contained in the inflatable container 102.

Figure 6:
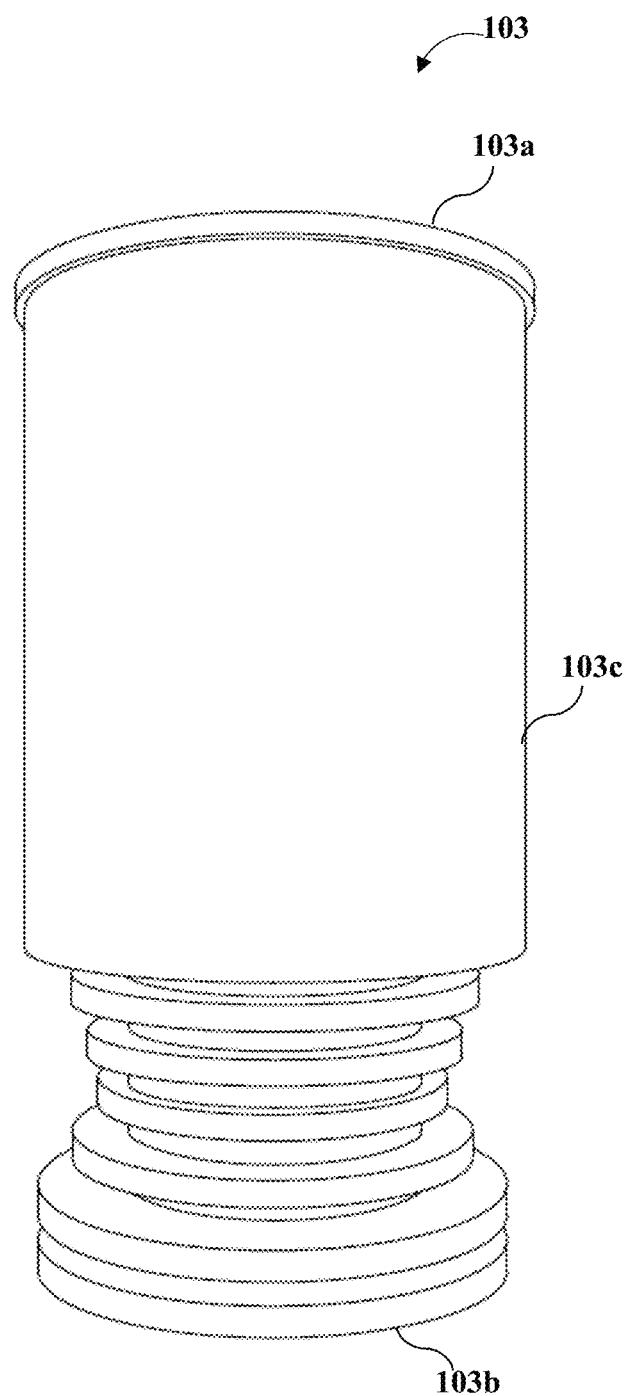
FIG. 6 illustrates the valve member of the inhalation system, according to an embodiment herein.

FIG. 6 illustrates the valve member 103 of the inhalation system 101 shown in FIG. 1, according to an embodiment herein. As illustrated in FIG. 6, in an embodiment, the valve member 103 comprising a cylindrically-shaped body 103c defined between a first opening 103a and a second opening 103b. The first opening 103a of the valve member 103 is configured to be connected to the open end of the fluid transfer member, for example, the inflatable container 102 illustrated in FIG. 2 and FIG. 9C, or the hose member 127 illustrated in FIG. 10. The second opening 103b of the valve member 103 is configured to be connected to the vaporizer 111 illustrated in FIG. 2 and FIGS. 9D-9E and to a mouthpiece 104 as illustrated in FIG. 1 and FIGS. 9F-9G. The valve member 103 is configured to be positioned atop the elongate nozzle 112 of the vaporizer 111 as illustrated in FIGS. 5A-5B, where the second opening 103b of the valve member 103 is positioned atop the upper section 111a of the vaporizer 111.

Figure 7A:
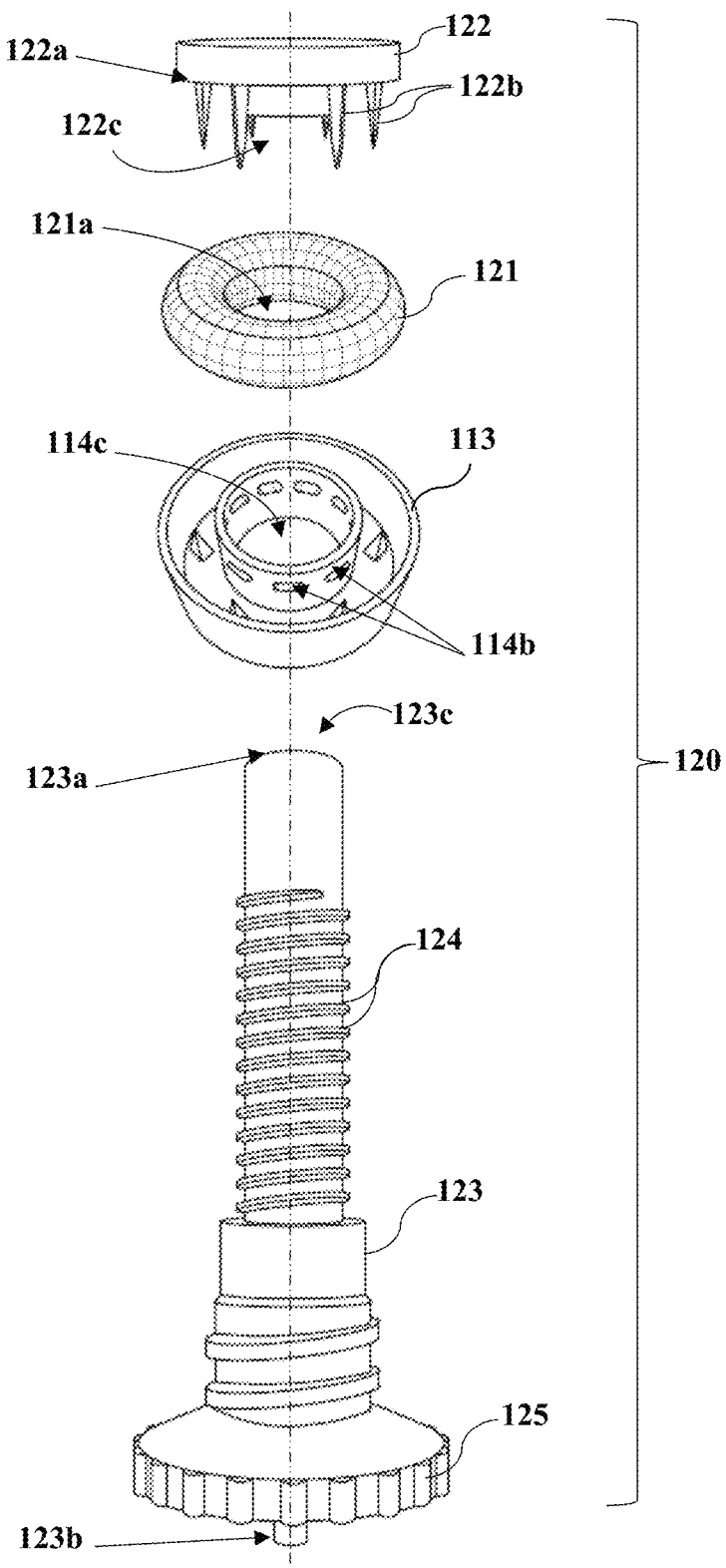
FIG. 7A illustrates an exploded view of the cartridge assembly of the inhalation system, according to an embodiment herein.

FIG. 7A illustrates an exploded view of the cartridge assembly 120 of the inhalation system 101 shown in FIG. 1, according to an embodiment herein. In an embodiment, the substance holder 121 and the cartridge 113 are configured as ring-shaped members comprising central openings 121a and 114c respectively. The substance holder 121 is made of, for example, plastic. The substance holder 121 contains the inhaling substance and/or the flavoring substance, for example, a fruit flavored liquid oil. In this embodiment, the cartridge assembly 120 comprises a stem member 123, a cartridge 113, and a cap member 122. The cartridge 113 accommodates the substance holder 121. The stem member 123 is configured to coaxially accommodate the cartridge 113 with the substance holder 121 through the central openings 114c and 121a of the cartridge 113 and the substance holder 121 respectively. The stem member 123 comprises an upper end 123a and a lower end 123b. The upper end 123a of the stem member 123 is connected to the open end 102a of the fluid transfer member, for example, the inflatable container 102 illustrated in FIG. 4 and FIGS. 9B-9C. In an embodiment, the stem member 123 is configured with a hollow center 123c. In an embodiment, the stem member 123 is twistably removed from the body 103c of the valve member 103 prior to connecting the second opening 103b of the valve member 103 to the vaporizer 111 shown in FIG. 2. The lower end 123b of the stem member 123 extends from a support base 125 of the stem member 123. In an embodiment, after vaporization of the inhaling substance and/or the flavoring substance and inflation of the inflatable container 102, the lower end 123b of the stem member 123 is connected to a non-locking mouthpiece 104 as illustrated in FIG. 1 and FIGS. 9F-9G. In an embodiment, the lower end 123b of the stem member 123 is configured as a non-locking mouthpiece. The lower end 123b of the stem member 123 receives and transfers the inhaling fluid flowing from the inflatable container 102 to a mouth of a user through the hollow center 123c of the stem member 123.

The cap member 122 is coaxially positioned on the stem member 123 through a central opening 122c of the cap member 122. The cap member 122 is suspended above the substance holder 121. In an embodiment, the cap member 122 comprises pins 122b extending downwardly from a lower surface 122a of the cap member 122. The pins 122b of the cap member 122 are configured to puncture the substance holder 121 and release the inhaling substance, for example, a flavoring substance, into the absorbent member (not shown) accommodated in the cartridge 113. When the cap member 122 with the pins 122b is screwed downwards to pierce the substance holder 121, the pins 122b seal the puncture holes in the substance holder 121, thereby plugging the puncture holes. Plugging the puncture holes by the pins 122b of the cap member 122 allows a minimal leak of the flavoring substance into the absorbent member, thereby causing the flavor of the flavoring substance to remain fresh and last long. The inhalation system 101, therefore, only needs a few drops, for example, about 10 to 15 drops of the flavoring substance to provide a user with an adequate amount of flavor for each vaporization session.

Figure 7B:
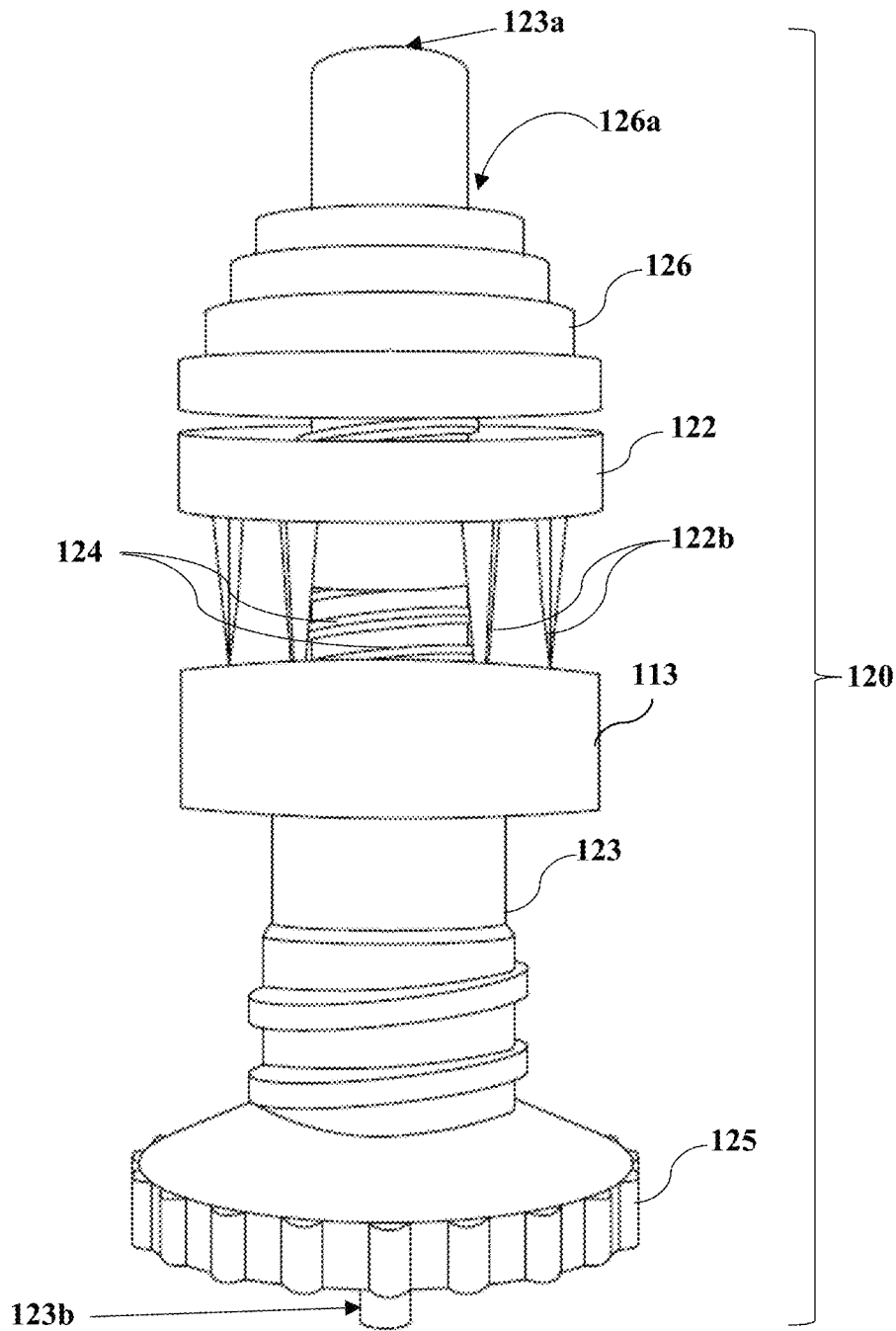
FIG. 7B illustrates an assembled view of the cartridge assembly of the inhalation system, according to an embodiment herein.

FIG. 7B illustrates an assembled view of the cartridge assembly 120 of the inhalation system 101, according to an embodiment herein. In an embodiment, the stem member 123 comprises screw threads 124 illustrated in FIG. 7A, that engage with internal threads (not shown) configured within the central opening 122c of the cap member 122. The stem member 123 is twisted to engage with and lock the cap member 122 to the stem member 123 as illustrated in FIG. 7B. The action of twisting the stem member 123 to remove the stem member 123 from the cartridge 113 causes the cap member 122 with the pins 122b to descend with the help of a collapsible spring member 126 that is positioned atop the cap member 122 and helps push the cap member 122 downwards. In an embodiment, the cartridge assembly 120 further comprises the collapsible spring member 126. The collapsible spring member 126 is coaxially positioned on the stem member 123 through a central opening 126a of the collapsible spring member 126. The collapsible spring member 126 is positioned above the cap member 122. The collapsible spring member 126 is configured to push the cap member 122 with the pins 122b downwards towards the substance holder 121 for puncturing the substance holder 121 and releasing the inhaling substance into the absorbent member accommodated in the cartridge 113. The collapsible spring member 126 is configured to create a funnel for harnessing the inhaling fluid into the fluid transfer member, for example, the inflatable container 102 shown in FIGS. 9C-9E, and for preventing waste from dissipating while passing through the cartridge assembly 120.

As the user twists and pulls the stem member 123 to remove the stem member 123 from the cartridge 113, the cap member 122 with the pins 122b punctures the substance holder 121 and releases the inhaling substance, for example, the flavored substance into the absorbent member that is positioned below the substance holder 121 in the cartridge 113. The user then positions the cartridge 113 atop of the vaporizer 111 for gentle heating to release the aroma of the flavored fluid that is captured inside of the inflatable container 102. After the inflatable container 102 fills with the flavored fluid, the user may remove the cartridge 113 from the vaporizer 111 and then reconnect the stem member 123 into the cartridge 113 by screwing the stem member 123 into place. The cap member 122 may then be pulled up to open or pushed down to close to provide access to the flavored fluid through the lower end 123b via the hollow center 123c of the stem member 123.

Figure 8A:
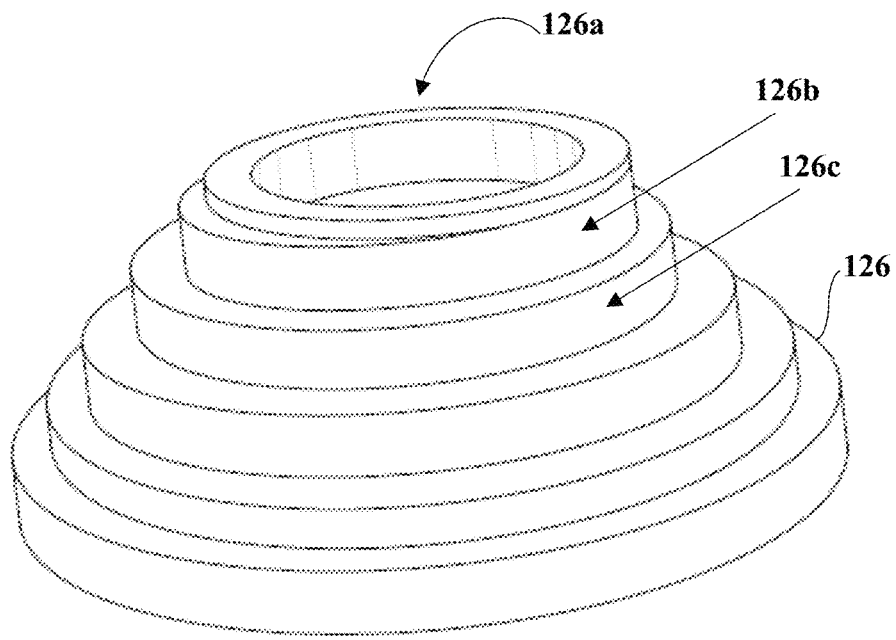
FIG. 8A illustrates a perspective view of a collapsible spring member of the cartridge assembly of the inhalation system in an extended position, according to an embodiment herein.
Figure 8B:
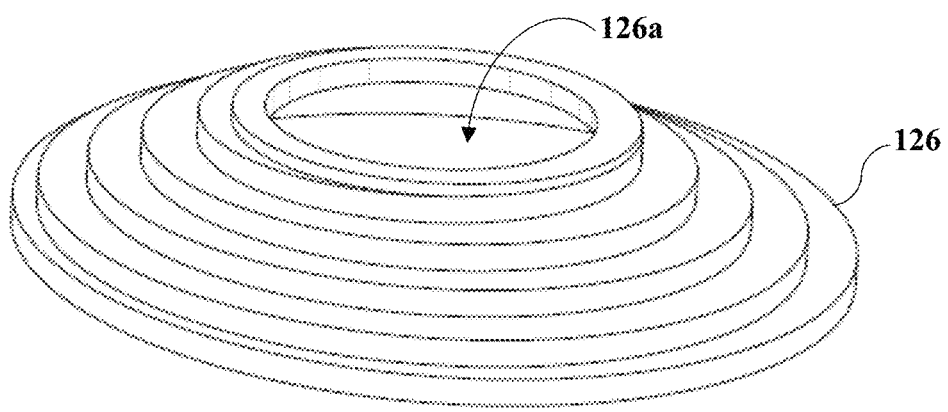
FIG. 8B illustrates a perspective view of a collapsible spring member of the cartridge assembly of the inhalation system in a collapsed position, according to an embodiment herein.

FIG. 8A illustrates a perspective view of the collapsible spring member 126 of the cartridge assembly 120 shown in FIG. 7B, in an extended position, according to an embodiment herein. In an embodiment, the collapsible spring member 126 is configured to collapse into a flat structure during compression to optimize space within the valve member 103 shown in FIGS. 3A-3B. In an extended position, the height of the collapsible spring member 126 is, for example, about 12.5 millimeters (mm). FIG. 8B illustrates a perspective view of the collapsible spring member 126 of the cartridge assembly 120 in a collapsed position, according to an embodiment herein. Each ring 126b of the collapsible spring member 126 collapses inside of a ring 126c immediately below to create a flat structure when fully compressed. In a collapsed positioned, the height of the collapsible spring member 126 is, for example, about 5 mm. The collapsible spring member 126 is configured to take up the least amount of space in the cartridge assembly 120, thereby creating a compact inhalation system 101 as shown in FIG. 1 and FIG. 9G.

Figure 9A:
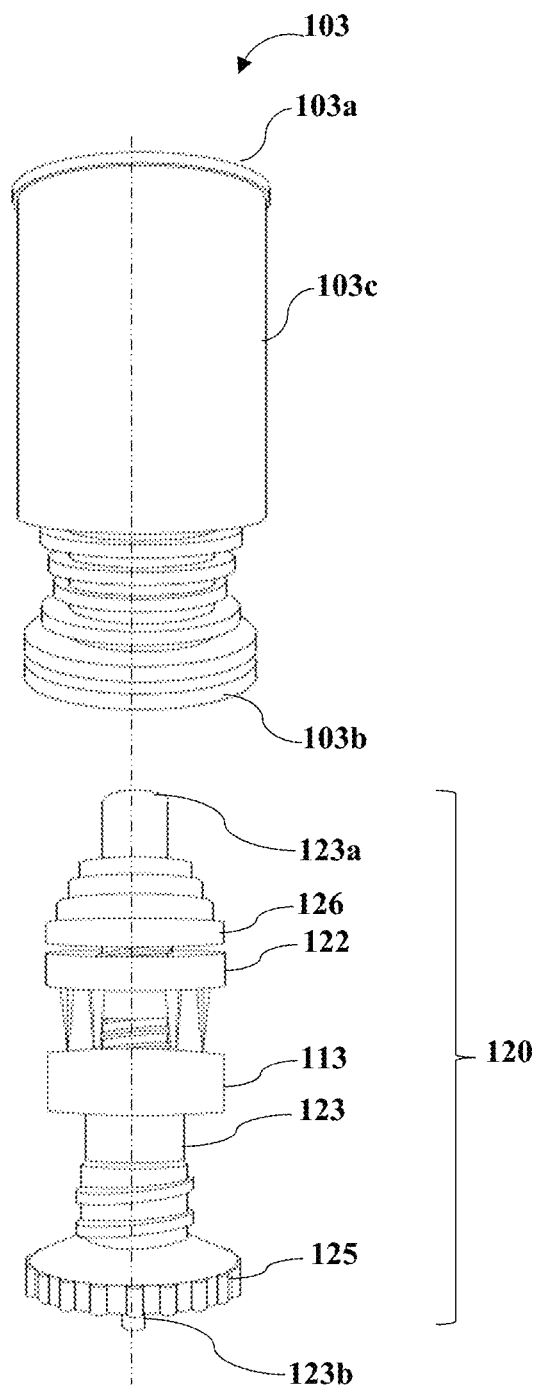
FIG. 9A illustrates a disassembled view of the valve member of the inhalation system, according to an embodiment herein.

FIG. 9A illustrates a disassembled view of the valve member 103 of the inhalation system 101 shown in FIG. 1, according to an embodiment herein. The cartridge assembly 120 is configured to be positioned within the body 103c of the valve member 103. The cartridge assembly 120 comprises the internal components, for example, the collapsible spring member 126, the cap member 122, the substance holder 121, the cartridge 113, the stem member 123, etc., illustrated in FIGS. 7A-7B, to be encompassed within the body 103c of the valve member 103.

Figure 9B:
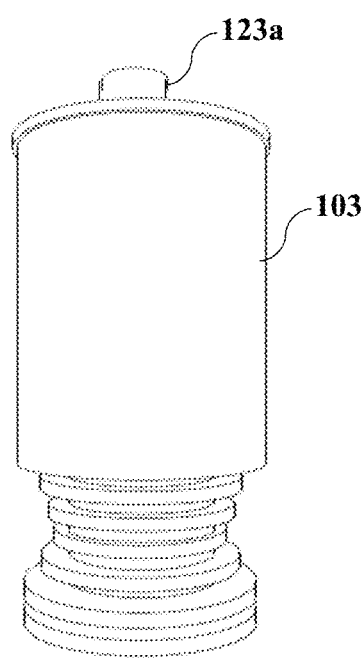
FIG. 9B illustrates an assembled view of the valve member of the inhalation system, according to an embodiment herein.

FIG. 9B illustrates an assembled view of the valve member 103 of the inhalation system 101 shown in FIG. 1, according to an embodiment herein. The valve member 103 encompasses and encloses the cartridge assembly 120 comprising the internal components, for example, the collapsible spring member 126, the cap member 122, the substance holder 121, the cartridge 113, the stem member 123, etc., illustrated in FIGS. 7A-7B. On assembling the valve member 103 over the cartridge assembly 120, the upper end 123a of the stem member 123 protrudes outwardly as illustrated in FIG. 9B.

Figure 9C:
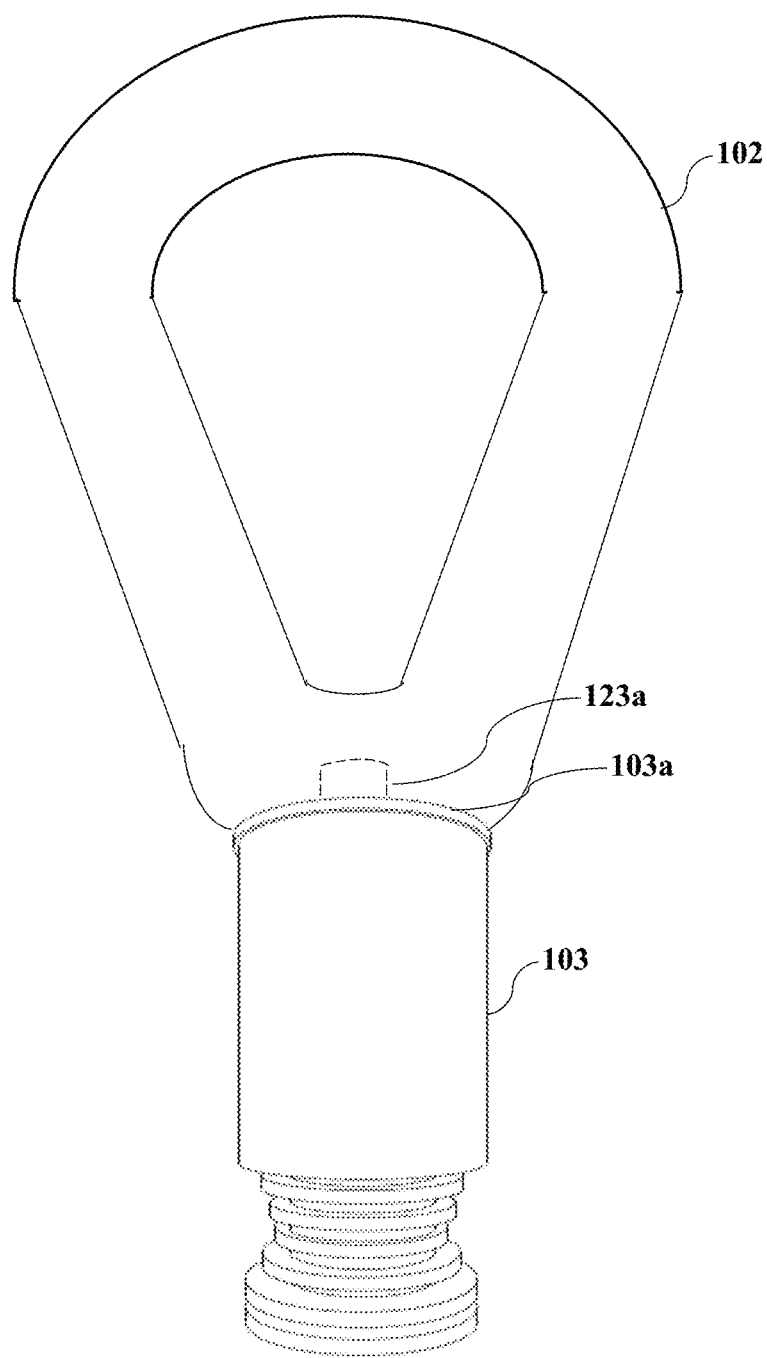
FIG. 9C illustrates a front view showing connection of a fluid transfer member to a first opening of the valve member, according to an embodiment herein.
Figure 10:
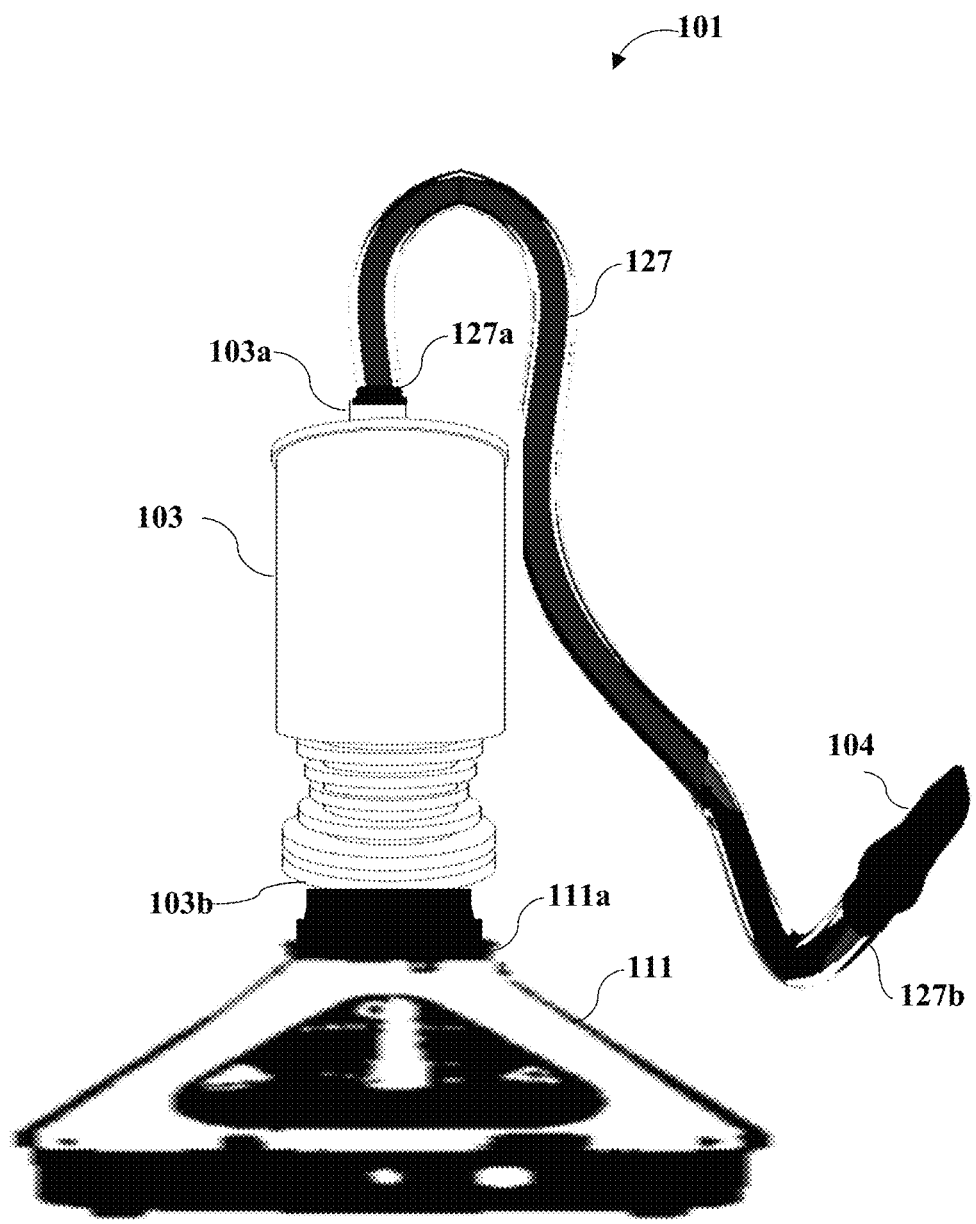
FIG. 10 illustrates a front view showing the fluid transfer member configured as a hose member and connected to a vaporizer via the valve member of the inhalation system, according to an embodiment herein.

FIG. 9C illustrates a front view showing connection of a fluid transfer member, for example, an inflatable container 102, to the first opening 103a of the valve member 103, according to an embodiment herein. The inflatable container 102 is positioned atop the first opening 103a of the valve member 103 over the upper end 123a of the stem member 123 as illustrated in FIG. 9C.

Figure 9D:
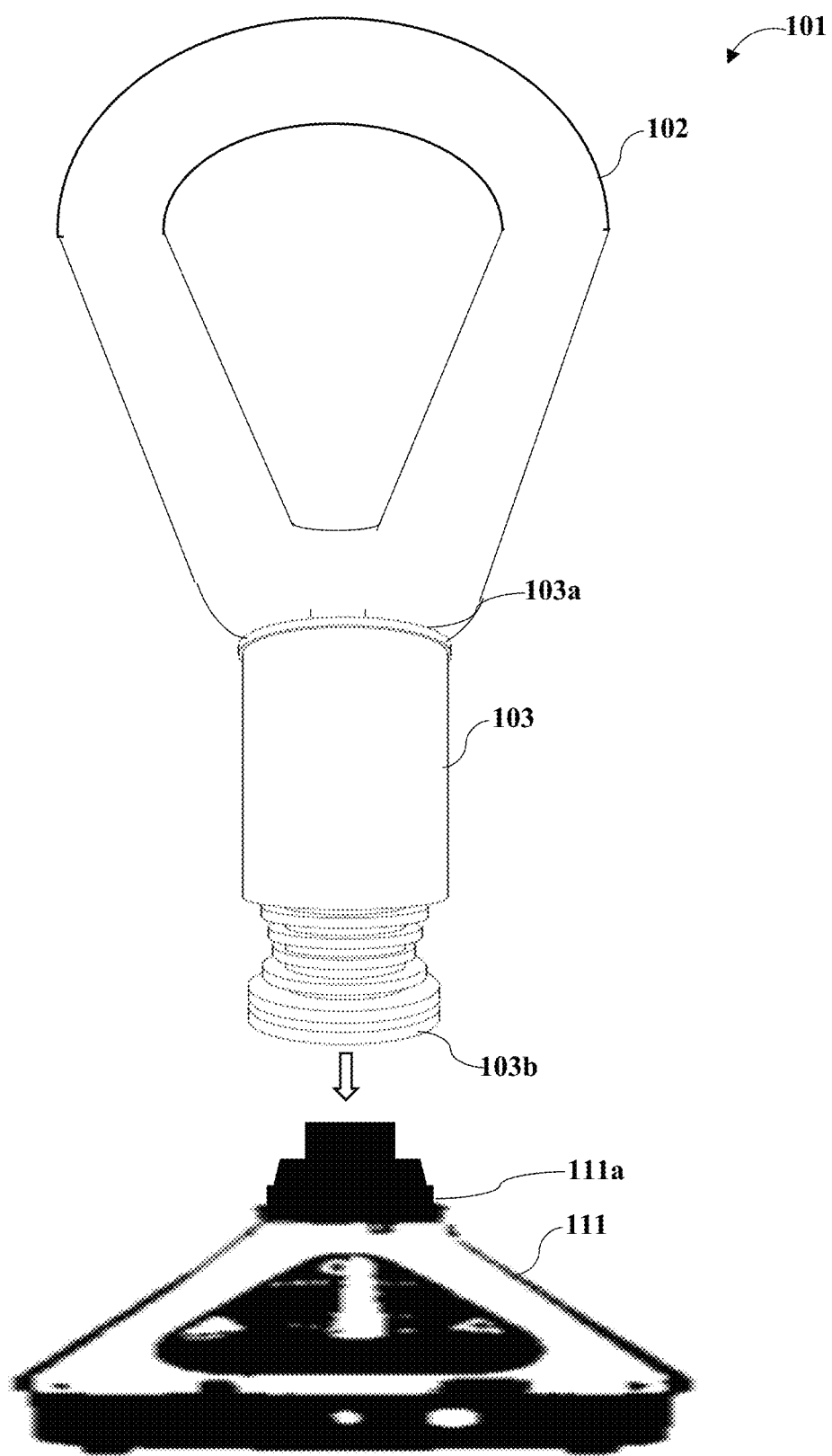
FIGS. 9D-9E illustrates front views of the inhalation system, showing connection of the assembled valve member to a vaporizer via a second opening of the valve member, according to an embodiment herein.
Figure 9E:
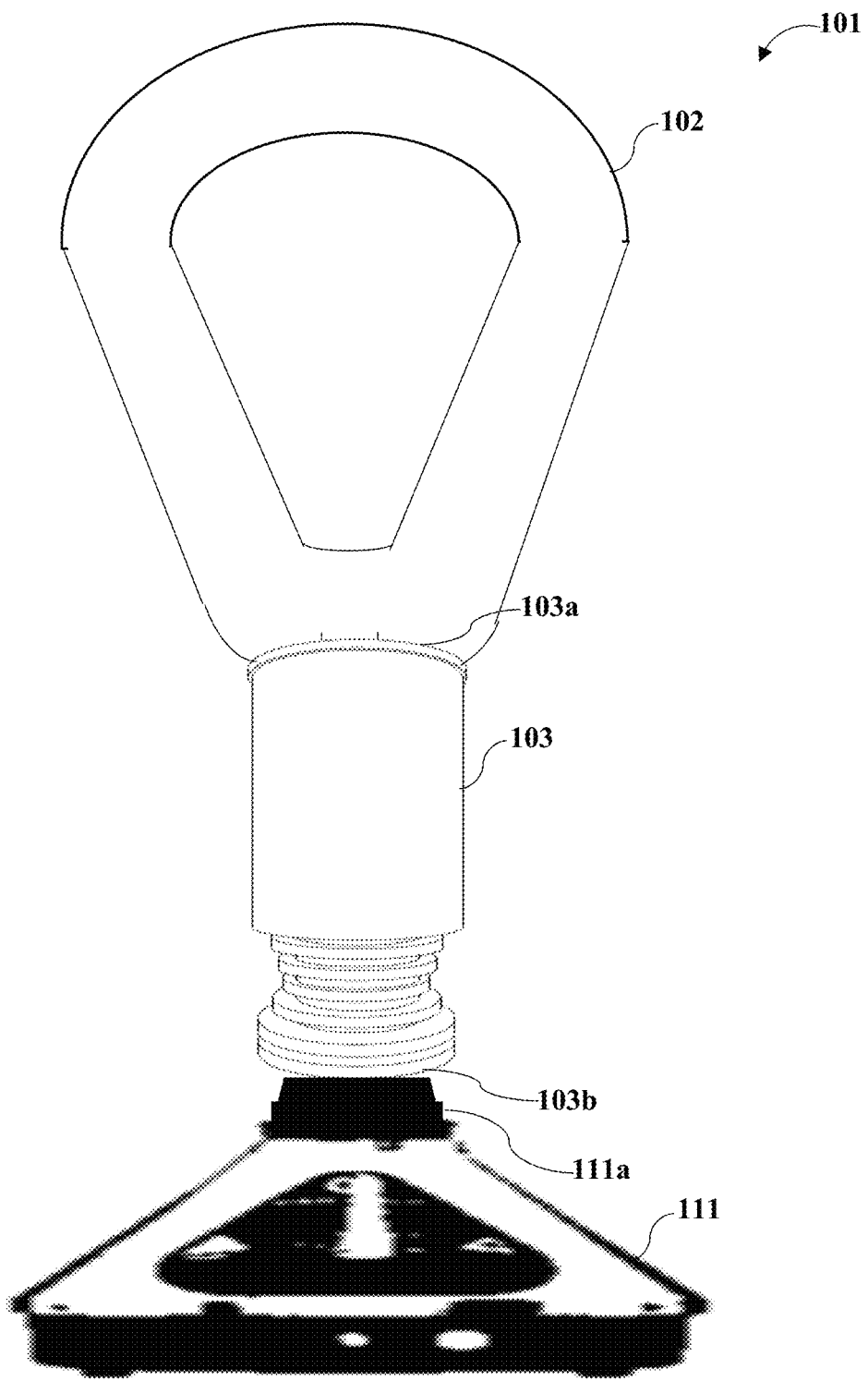
Figure 9F:
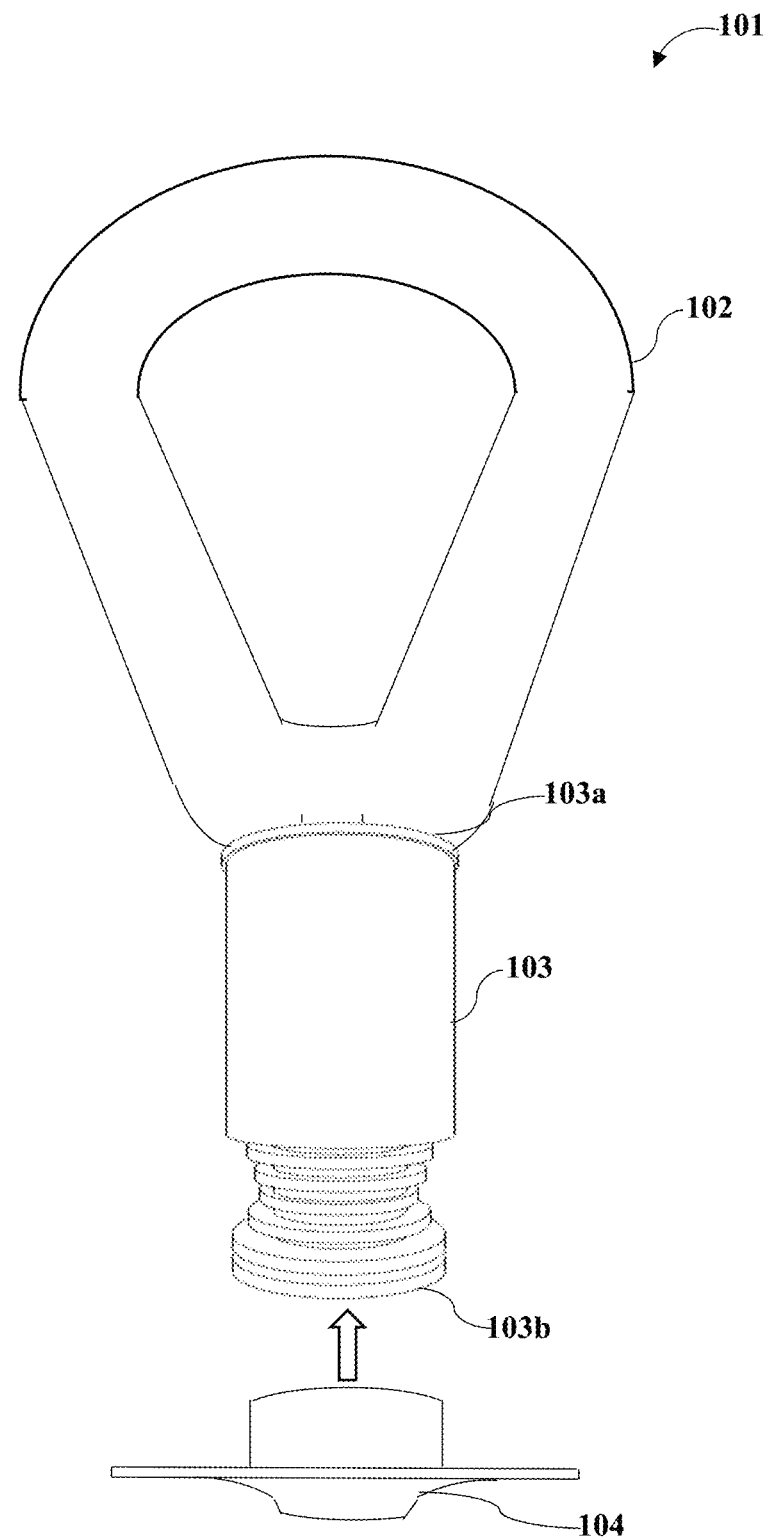
FIGS. 9F-9G illustrate front views of the inhalation system, showing connection of the assembled valve member to a mouthpiece via the second opening of the valve member, according to an embodiment herein.
Figure 9G:
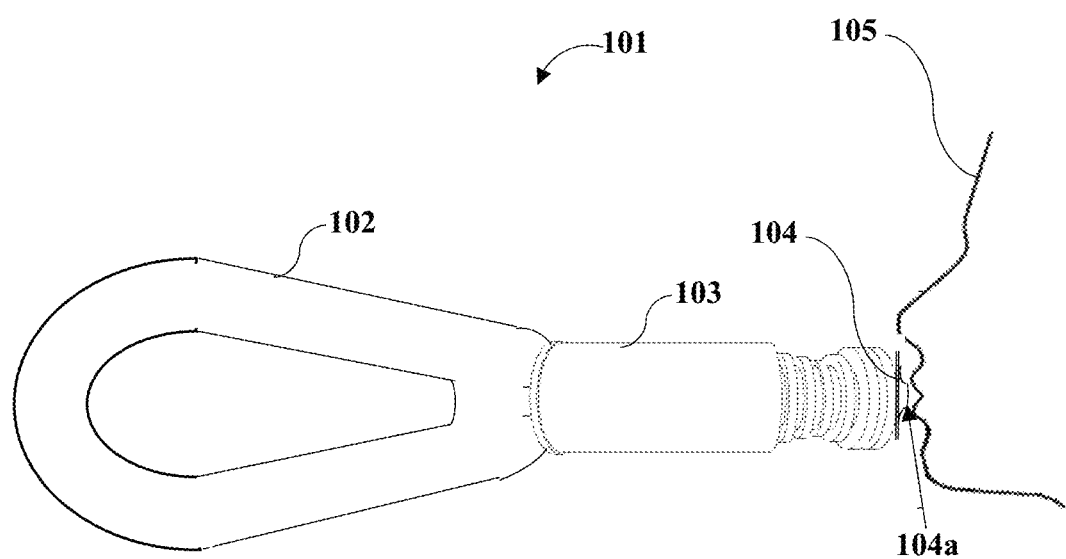

FIGS. 9D-9E illustrate front views of the inhalation system 101, showing connection of the assembled valve member 103 to a vaporizer 111 via the second opening 103b of the valve member 103, according to an embodiment herein. The second opening 103b of the valve member 103 is positioned atop the upper section 111a of the vaporizer 111 as illustrated in FIG. 9E. The inflatable container 102 is configured to inflate and contain the inhaling fluid received from the cartridge assembly 120 illustrated in FIG. 9A, in communication with the vaporizer 111.

FIGS. 9F-9G illustrate front views of the inhalation system 101, showing connection of the assembled valve member 103 to a mouthpiece 104 via the second opening 103b of the valve member 103, according to an embodiment herein. After the vaporizer 111 fills the fluid transfer member, for example, the inflatable container 102 with the inhaling fluid or the flavored inhaling fluid, the second opening 103b of the valve member 103 is disconnected from the upper section 111a of the vaporizer 111 and connected to a mouthpiece 104 as illustrated in FIG. 9F. The mouthpiece 104 is operably connected to the cartridge assembly 120 illustrated in FIG. 9A, via the second opening 103b of the valve member 103. The mouthpiece 104 connects to the lower end 123b of the stem member 123 illustrated in FIG. 9A via the second opening 103b of the valve member 103. A user 105 then places a tip 104a of the mouthpiece 104 near the user's 105 mouth and inhales the inhaling fluid or the flavored inhaling fluid extracted from the inflatable container 102 through the mouthpiece 104 as illustrated in FIG. 9G.

FIG. 10 illustrates a front view showing the fluid transfer member configured as a hose member 127 and connected to a vaporizer 111 via the valve member 103 of the inhalation system 101, according to an embodiment herein. In this embodiment, the fluid transfer member is a hose member 127 comprising an open first end 127a and an open second end 127b. The hose member 127 is, for example, made of a silicone material. In this embodiment, the open first end 127a of the hose member 127 is operably connected to the first opening 103a of the valve member 103, while the second opening 103b of the valve member 103 remains connected to the vaporizer 111. Moreover, in this embodiment, the open second end 127b of the hose member 127, that is distal to the open first end 127a of the hose member 127, is operably connected to the mouthpiece 104. The hose member 127 is configured to transfer the inhaling fluid or the flavored inhaling fluid received from the cartridge assembly 120 illustrated in FIG. 9A, in communication with the vaporizer 111, to a user's mouth via the mouthpiece 104. In this embodiment, the user may choose to bypass the inflatable container 102 illustrated in FIGS. 9D-9E and inhale the inhaling fluid or the flavored inhaling fluid directly from the valve member 103 by using the hose member 127 that may be attached to the first opening 103a of the valve member 103 with the opposite end 127b of the hose member 127 attached to the mouthpiece 104 for direct inhalation into the mouth.

Figure 11A:
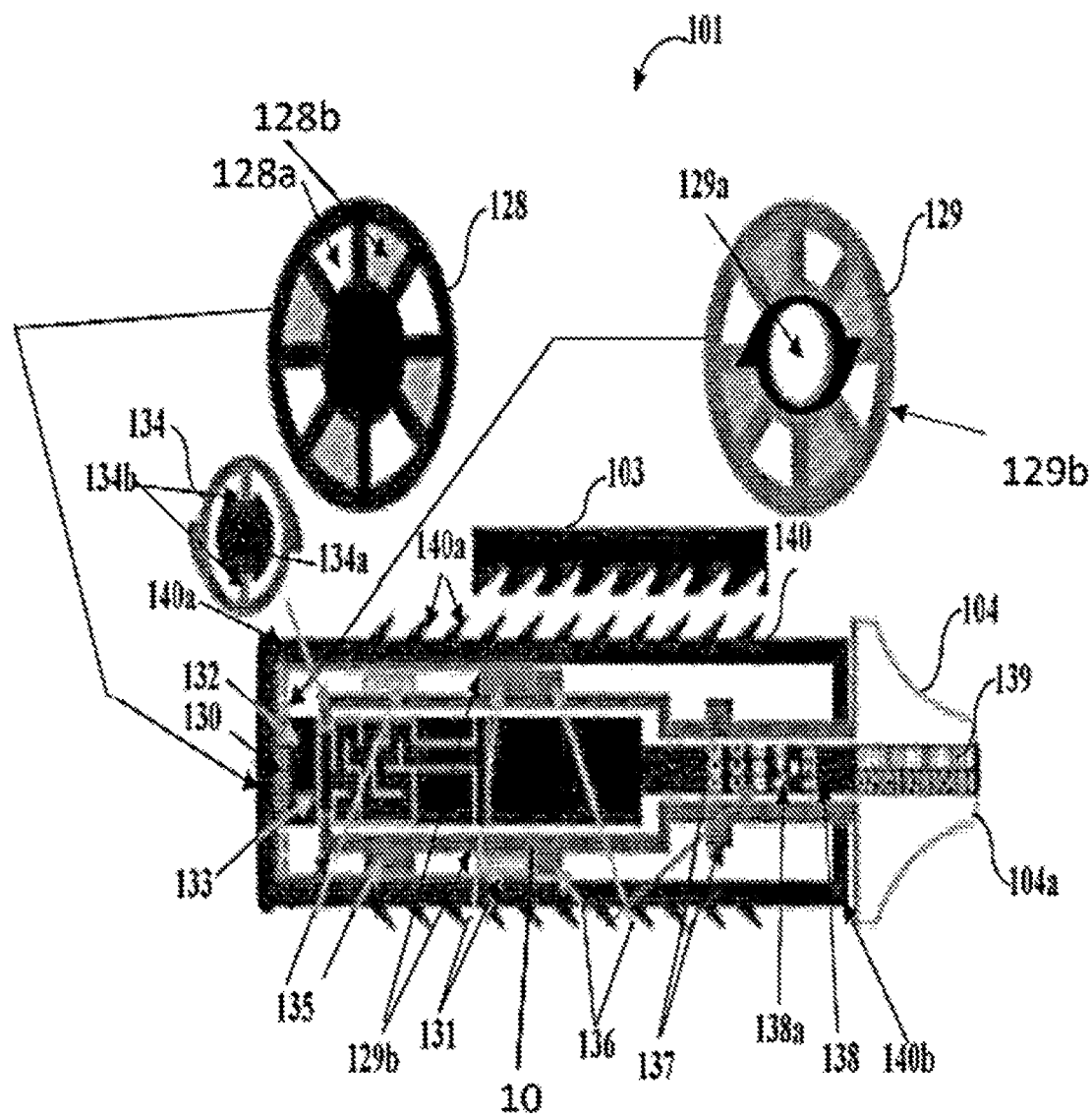
FIGS. 11A-11B illustrate partial cross-sectional views of the valve member configured as a locking mouthpiece assembly, according to an embodiment herein.
Figure 11B:
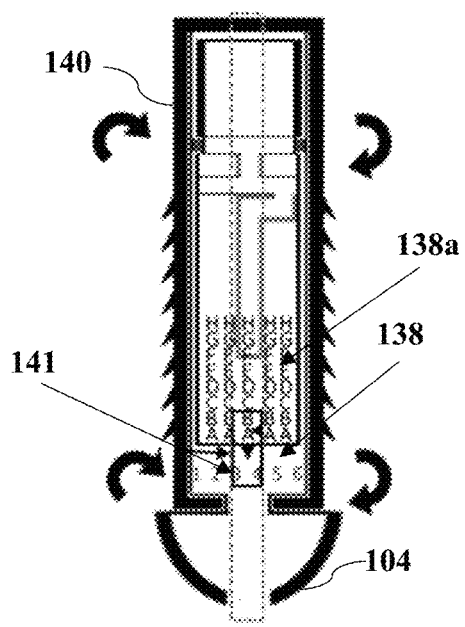

FIGS. 11A-11B illustrate partial cross-sectional views of the valve member 103 configured as a locking mouthpiece assembly, according to an embodiment herein. In an embodiment, the valve member 103 is configured as a combination lock pull-push bottle cap. The valve member 103 is configured to prevent unauthorized access to the contents of the fluid transfer member, for example, the inflatable container 102 illustrated in FIG. 1. In an embodiment, the valve member 103 is implemented in asthma or other gas medicine dispensers for use by asthmatic patients. The valve member 103 prevents access to the inhaling fluid, for example, medicinal fluid, etc., until a user successfully navigates through the valve member 103. In an embodiment, the valve member 103 is operably connected to the cartridge 113 illustrated in FIGS. 5A-5B or to the cartridge assembly 120 illustrated in FIGS. 7A-7B via the second opening 103b of the valve member 103 illustrated in FIG. 1. The valve member 103 configured as a locking mouthpiece assembly receives and transfers the inhaling fluid flowing from the inflatable container 102 to a user's mouth via the mouthpiece 104 as illustrated in FIG. 1. The valve member 103 configured as the locking mouthpiece assembly is configured to allow authentication of the user prior to releasing the inhaling fluid to the user's mouth via the mouthpiece 104. In this embodiment, to implement the locking mouthpiece assembly, the valve member 103 comprises an enclosure 140, a first flywheel 128, a stabilization pin 132, a second flywheel 129, and a cylindrical member 134. In an embodiment, the enclosure 140 is a tubular shaped plastic encasing. In an embodiment, ratchet teeth 140a are externally configured on the enclosure 140. The ratchet teeth 140a of the enclosure 140 are configured to engage with internal grooves or mating ratchet teeth of another container or the valve member 103.

The enclosure 140 comprises a first end 140a and a second end 140b. The first flywheel 128 is built into the first end 140a of the enclosure 140. The first flywheel 128 comprises passageways white open airway passage 128a and grey closed airway passage 128b, for example, air passageways, in fluid communication with the first opening 103a of the valve member 103 for allowing flow of the inhaling fluid from the inflatable container 102 into the enclosure 140 and out to the mouthpiece 104. The stabilization pin 132 is attached to the first flywheel 128 and positioned within the enclosure 140. The stabilization pin 132 extends from the first flywheel 128 to a tip 104a of the mouthpiece 104. The stabilization pin 132 spans the entirety of the enclosure 140 and protrudes through the center of the mouthpiece 104. The stabilization pin 132 is configured with an inscribing scroll for inscribing a randomly generated bidirectional path 133 and one or more identification elements 139 thereon. The bidirectional path 133 is configured as an omnidirectional maze comprising bidirectional pathways or corridors that are positioned in a north direction, a south direction, an east direction, and a west direction. The stabilization pin 132 with the inscribing scroll is movable in an upward direction and a downward direction or in a left direction and a right direction. In an embodiment, the bidirectional path 133 is unique for each inhalation system 101 and is inscribed on both sides of the inscribing scroll 10. In an embodiment, the stabilization pin 132 is configured as an inscribing scroll for the locking mouthpiece assembly and the identification elements 139 inscribed or printed thereon. The identification elements 139, for example, barcodes, serial numbers, etc., are configured to identify the inhalation system 101 shown in FIG. 1. The barcodes are, for example, matrix barcodes or two-dimensional barcodes. In an embodiment, the identification elements 139 are configured to be input into the mobile application 109 deployed on the user device 107 shown in FIG. 1.

In an embodiment, the second flywheel 129 is configured as an internal closing flywheel with a central opening 129a. The second flywheel 129 is wrapped around the stabilization pin 132 through the central opening 129a. In an embodiment, the second flywheel 129 spans halfway up the stabilization pin 132. The stabilization pin 132 is inserted through the central opening 129a of the second flywheel 129. The second flywheel 129 is as wide as the internal circumference of the enclosure 140. The second flywheel 129 comprises a base flywheel 130 positioned below the second flywheel 129 and tab elements 131 at an upper end 129b of the second flywheel 129 for twisting the second flywheel 129 to open and close the passageways 128a and 128b of the first flywheel 128 as required. The second flywheel 129 and the cylindrical member 134 of the valve member 103 are positioned coaxially around the stabilization pin 132. The second flywheel 129 and the cylindrical member 134 operably communicate with each other for opening and closing the passageways 128a and 128b of the first flywheel 128 and controlling access to the inhaling fluid in the inflatable container 102. In an embodiment, the cylindrical member 134 is configured as an air cylinder with a central opening 134a. The cylindrical member 134 is wrapped around the stabilization pin 132 through the central opening 134a and extends along a length of the stabilization pin 132. The stabilization pin 132 is inserted through the central opening 134a of the cylindrical member 134. The cylindrical member 134 comprises track pins 134b configured to navigate through the bidirectional path 133 along the inscribing scroll to unlock the valve member 103. In an embodiment, the inhalation system 101 further comprises tab elements 131 and 135, 136 positioned on one end of the second flywheel 129 and on one end of the cylindrical member 134 respectively. The tab elements 135 are configured to rotate or turn the second flywheel 129. The tab elements 136 are configured as stop tabs to close the first flywheel 128 during transit and storage of the inhalation system 101. The tab elements 131 and 135, 136 of the second flywheel 129 and the cylindrical member 134 respectively, are in operable communication for opening and closing the passageways 128a and 128b of the first flywheel 128. In another embodiment, the inhalation system 101 further comprises tab elements 137 positioned on the cylindrical member 134 for precluding the cylindrical member 134 from moving a substantial distance around the stabilization pin 132 within the enclosure 140. In an embodiment, the tab elements 137 are configured as stop tabs to prevent internal damage to the valve member 103 during pullup of the mouthpiece 104.

In an embodiment, a display area 138 is positioned on the stabilization pin 132 for displaying authentication elements 138a, for example, combination lock letters and numerals, along an X-axis and a Y-axis as illustrated in FIG. 11A. For example, numerals are inscribed along the X-axis in the display area 138, and letters are inscribed along the Y-axis in the display area 138. In an embodiment, the display area 138 is positioned proximal to the mouthpiece 104. The letters along the Y-axis are repeated inline horizontally to allow viewing by a user as the user twists, turns, and moves the cylindrical member 134 up and down to navigate the bidirectional path 133 inscribed on the inscribing scroll 10. In an embodiment, the enclosure 140 of the valve member 103 comprises a window 141 configured to allow viewing of the authentication elements 138a inscribed on the stabilization pin 132 as illustrated in FIG. 11B. In an embodiment, the window 141 is made of a transparent material that allows clear viewing of the authentication elements 138a along the X-axis and the Y-axis.

The mouthpiece 104 is operably connected to the second end 140b of the enclosure 140. In an embodiment, the mouthpiece 104 is positioned proximal to the display area 138. In an embodiment, the mouthpiece 104 is made of a transparent plastic material. The mouthpiece 104 is configured to receive and transfer the inhaling fluid flowing from the enclosure 140 to the user's mouth. To unlock the valve member 103, the user must successfully navigate the track pins 134b of the cylindrical member 134 through the bidirectional path 133 by using an authentication code, for example, a predefined combination of letters and numerals, for moving north and south directions and east and west directions along the inscribing scroll. When the combination of movements reaches the end, the user has successfully unlocked the valve member 103. The user may then twist the mouthpiece 104 to cause the tab elements 135 and 136 on either side of the cylindrical member 134 with the track pins 134b to engage with the tab elements 131 on the second flywheel 129 to twist and open the passageways 128a and 128b of the first flywheel 128 and gain access to the inhaling fluid within the inflatable container 102.

Consider an example where the mobile application in communication with the authentication server displays an authentication code comprising a combination of characters, that is, numbers and letters, for example, 7,C,5,D,7,H,14 to unlock the valve member 103 and the number 7 to lock the valve member 103. The window 141 exposes the authentication elements 138a, that is, the numbers and letters, inscribed on the stabilization pin 132 and the inscribing scroll. A user twists and aligns the valve member 103 with respect to an arrow displayed on the display area 138 of the valve member 103 as illustrated in FIG. 11B for selecting the characters of the authentication code. The user then twists and aligns the valve member 103 with grooves, performs one slight tug towards themselves, and then follows the next groove until the next character in the authentication code is reached. The user then performs another tug towards themselves and twists the valve member 103 along the grooves to align with the next character in the authentication code. The user then performs another tug towards themselves and repeats the above process until the valve member 103 is unlocked. In this manner, the user navigates the bidirectional path 133 inscribed on the stabilization pin 132 and defined by the authentication code.

Figure 12:
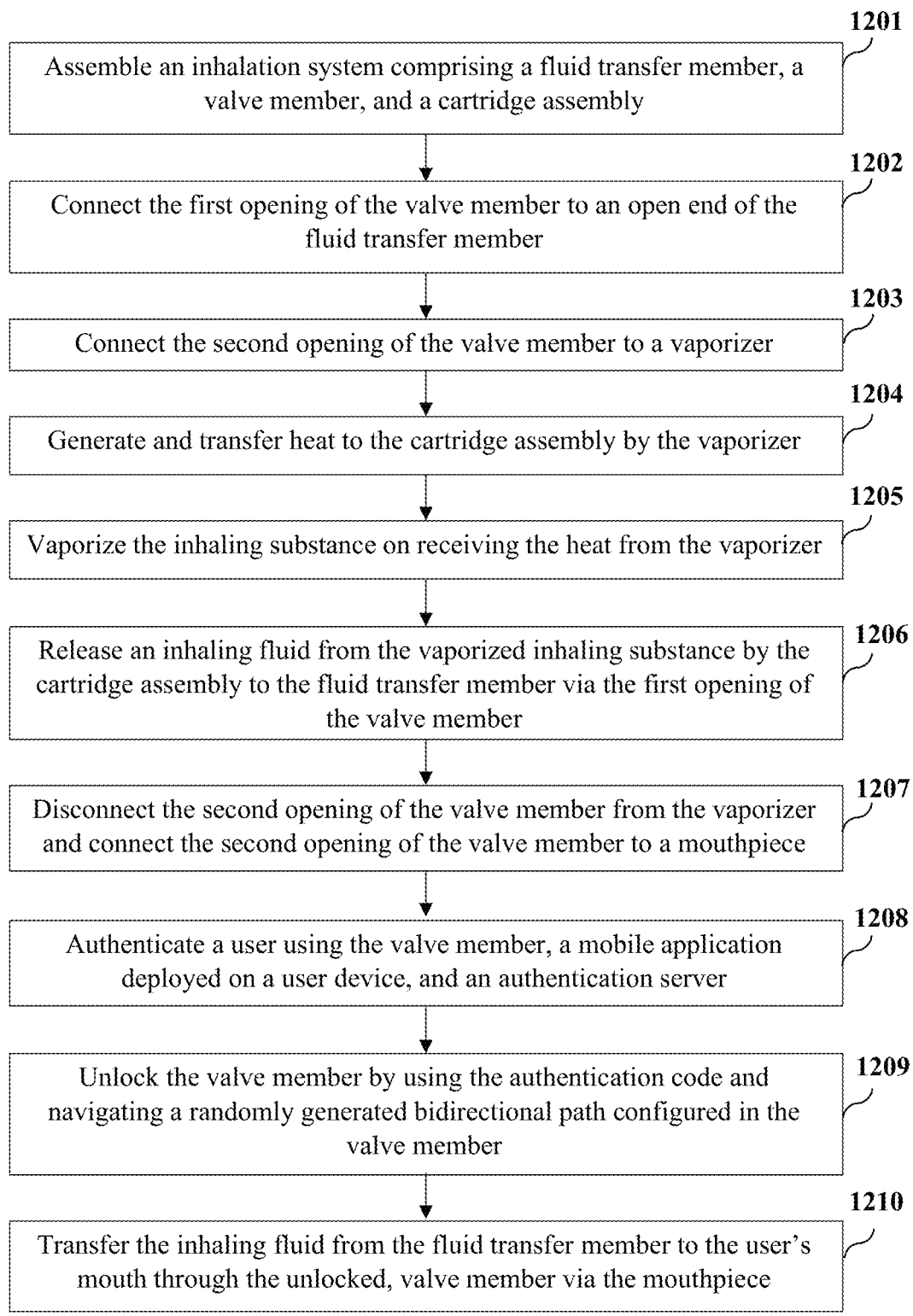
FIG. 12 illustrates a method for providing and using the inhalation system with user authentication, according to an embodiment herein.

FIG. 12 illustrates a method for providing and using the inhalation system with user authentication, according to an embodiment herein. In the method disclosed herein, the inhalation system 101 comprising the fluid transfer member, for example, the inflatable container 102, the valve member 103 configured as a locking mouthpiece assembly, and the cartridge assembly 120 as disclosed in the detailed description of FIGS. 1-9G and FIGS. 11A-11B, is assembled 1201. Furthermore, in the method disclosed herein, a user connects 1202 the first opening of the valve member to an open end of the fluid transfer member, for example, a balloon, and connects 1203 the second opening of the valve member to a vaporizer. The vaporizer generates and transfers 1204 heat to the cartridge assembly positioned within the body of the valve member. The generated and transferred heat heats the absorbent member with the inhaling substance received from the substance holder to a temperature lower than a combustible temperature of the inhaling substance. On receiving the heat from the vaporizer, the inhaling substance received from the substance holder by the absorbent member of the cartridge assembly is vaporized 1205. The cartridge assembly releases 1206 an inhaling fluid from the vaporized inhaling substance to the fluid transfer member via the first opening of the valve member. The fluid transfer member receives and contains the inhaling fluid therewithin. The user then disconnects 1207 the second opening of the valve member from the vaporizer and connects the second opening of the valve member to a mouthpiece.

In an embodiment, the user is authenticated 1208 using the valve member configured as a locking mouthpiece assembly, the mobile application deployed on a user device, and a remote server also referred to as the authentication server, as follows: The mobile application requests the user to enter or scan identification elements, for example, barcodes, serial numbers, etc., inscribed on the inhalation system. When the user enters or scans the identification elements of the inhalation system into the mobile application on the user device, the mobile application communicates the identification elements to the authentication server via a network, for example, the internet. The mobile application then requests the user to scan an identification element of the user, for example, a driver's license of the user. When the user scans the user's identification element into the mobile application, the mobile application communicates the identification element to the authentication server via the network. The mobile application then requests the user to capture the user's image along with the user's identification element. When the user captures the image along with the user's identification element, the mobile application communicates the user's image along with the identification element of the user to the authentication server via the network. In an embodiment, the authentication server verifies identification information of the user by executing a facial recognition technique on the image and the identification element. The mobile application then requests the user to input the user's biometric information, for example, a fingerprint, retinal scan, facial recognition, etc., When the user inputs the biometric information into the mobile application, the mobile application communicates the biometric information to the authentication server via the network. On successful verification of the identification elements of the, eye system, the identification information of the user, and the biometric information of the user by the authentication server, the mobile application receives an authentication code comprising a predefined combination of the authentication elements associated with the inhalation system from the authentication server via the network for navigating the randomly generated bidirectional path and unlocking the valve member. The window in the enclosure of the valve member allows the user to view the authentication elements inscribed on the stabilization pin. The user unlocks 1209 the valve member by using the authentication code and navigating the randomly generated bidirectional path configured in the valve member. The unlocked, valve member then transfers 1210 the inhaling fluid from the fluid transfer member to the user's mouth via the mouthpiece.

The inhalation system disclosed herein is not shipped with an authentication code or pathway combinations included in the same packaging. The user is required to unlock the valve member using the dynamically generated authentication code comprising, for example, a combination of bidirectional numbers and letters, received from the mobile application after successful verification and authentication procedures disclosed above. Consider an example where a user purchases the inhalation system comprising the valve member configured as a locking mouthpiece assembly. The valve member comprises an identification element, for example, a barcode or a serial number. The user may scan or manually enter the identification element into the mobile application deployed on the user device. The mobile application communicates with the authentication server via a network, for example, the internet, and verifies the identification information embedded in the scanned barcode or the manually entered serial number against a database of the authentication server.

If the barcode or the serial number of the inhalation system is successfully located in the database, the mobile application, in communication with the authentication server via the network, prompts the user to scan a personal identification element or an identification card, for example, a state or government issued identification card or a driver's license. When the user positions the identification card on a display interface of the user device to be read by a card scanner of the user device, the mobile application automatically scans the identification card. After the identification card is successfully scanned, the mobile application transmits the identification information embedded in the scanned identification card to an authorizing entity, for example, a database of the Department of Motor Vehicles or other databases, via the network for instant verification and determination of the validity of the identification card. If successfully verified, the user may then proceed to the next authentication level implemented by the mobile application. In the next authentication level, the mobile application prompts the user to capture a self-image holding the identification card adjacent to the user's face. Once the image is captured, the user may then submit the captured image into the mobile application. The mobile application transmits the captured image to the authentication server via the network. In an embodiment, the authentication server executes a facial recognition technique for determining whether the user's image and a photograph of the user in the identification card are identical. If there is a match between the user's image and the photograph of the user, then the mobile application, in communication with the authentication server via the network, transmits a notification of the successful verification on a display interface of the user device. The method disclosed herein confirms the identity of the user remotely and in real-time using their identification card and facial recognition technology.

In an embodiment, the mobile application executes another authentication level and prompts the user to place the user's thumb or other finger on the display interface of the user device in a predefined location within the mobile application. The mobile application scans the user's fingerprint and stores the scanned fingerprint in the user device and in a database record of the authentication server. The authentication server stores the identification information of each user in the database and encrypts the identification information for privacy. The authentication server generates and transmits an authentication code to the mobile application via the network. The mobile application displays the authentication code on the display interface within the mobile application. When the user needs to gain access to another inhalation system with a valve member configured as a locked mouthpiece assembly, the user merely needs to scan the barcode or manually enter the serial number of the other inhalation system. Once the barcode or the serial number is verified by the authentication server, the mobile application prompts the user to place their finger on the display interface of the user device from where the user's fingerprint is read and verified. If the user's fingerprint is verified successfully, in communication with the authentication server, the mobile application displays the authentication code on the display interface within the mobile application. The user must follow a combination contained in the authentication code which provides a usage of numbers on the X-axis and letters on the Y-axis of the valve member. Upon following the combination of a series of pushes, pulls, twists, and turns, the user navigates the omnidirectional maze defined by the bio-direction path successfully on each side of the cylindrical member until the valve member is unlocked, thereby allowing access to the inhaling fluid inside of the inflatable container connected to the valve member. The above-recited authentication levels are useful, for example, to medical cannabis dispensaries allowing them to maintain compliance with state regulations. The valve member configured as a locking mouthpiece assembly and the method disclosed herein are also useful to users of prescribed medicine devices such as asthmatic medicine devices as the locking mouthpiece assembly and user authentication provide access to medicines only by authorized users who have the authentication code required to unlock the valve member.

The embodiments disclosed herein are configured to operate in a network environment comprising one or more computers that are in communication with one or more user devices via a network. In an embodiment, the computers communicate with the user devices directly or indirectly, via a wired medium or a wireless medium such as the Internet, a local area network (LAN), a wide area network (WAN) or the Ethernet, a token ring, or via any appropriate communications mediums or combination of communications mediums. Each of the user devices comprises processors that are adapted to communicate with the computers. In an embodiment, each of the computers is equipped with a network communication device, for example, a network interface card, a modem, or other network connection device suitable for connecting to the network. Each of the computers and the user devices executes an operating system. While the operating system may differ depending on the type of computer, the operating system provides the appropriate communications protocols to establish communication links with the network. Any number and type of machines may be in communication with the computers.

The embodiments disclosed herein are not limited to a particular computer system platform, processor, operating system, or network. One or more of the embodiments disclosed herein are distributed among one or more computer systems, for example, servers configured to provide one or more services to one or more user devices, or to perform a complete task in a distributed system. For example, one or more of embodiments disclosed herein are performed on a client-server system that comprises components distributed among one or more server systems that perform multiple functions according to various embodiments. These components comprise, for example, executable, intermediate, or interpreted code, which communicate over the network using a communication protocol. The embodiments disclosed herein are not limited to be executable on any particular system or group of systems, and are not limited to any particular distributed architecture, network, or communication protocol.

The foregoing examples and illustrative implementations of various embodiments have been provided merely for explanation and are in no way to be construed as limiting of the embodiments disclosed herein. While the embodiments have been described with reference to various illustrative implementations, drawings, and techniques, it is understood that the words, which have been used herein, are words of description and illustration, rather than words of limitation. Furthermore, although the embodiments have been described herein with reference to particular means, materials, techniques, and implementations, the embodiments herein are not intended to be limited to the particulars disclosed herein; rather, the embodiments extend to all functionally equivalent structures, methods and uses, such as are within the scope of the appended claims. It will be understood by those skilled in the art, having the benefit of the teachings of this specification, that the embodiments disclosed herein are capable of modifications and other embodiments may be effected and changes may be made thereto, without departing from the scope and spirit of the embodiments disclosed herein.

What is claimed is:

1. An inhalation system comprising:
   a fluid transfer member comprising an open first end configured to receive an inhaling fluid;
   a valve member operably connected to the open first end of the fluid transfer member, wherein the valve member comprises a body, a first opening, and a second opening, wherein the first opening is configured to be connected to the open first end of the fluid transfer member, and wherein the second opening is configured to be connected to a mouthpiece and a vaporizer;
   a cartridge assembly positioned within the body of the valve member, wherein the cartridge assembly comprises:
      a substance holder configured to contain an inhaling substance;
      an absorbent member positioned proximal to the substance holder, wherein the absorbent member is configured to absorb the inhaling substance received from the substance holder; and
      a cartridge configured to accommodate the substance holder and the absorbent member, wherein, when the second opening of the valve member is connected to the vaporizer, the vaporizer is configured to heat the absorbent member with the absorbed inhaling substance to a temperature lower than a combustible temperature of the inhaling substance for vaporizing the inhaling substance and releasing the inhaling fluid into the fluid transfer member; and
      the mouthpiece operably connected to the cartridge assembly via the second opening of the valve member, wherein the valve member is configured to receive and transfer the inhaling fluid flowing from the fluid transfer member to a mouth of a user via the mouthpiece,
   wherein the fluid transfer member is an inflatable container configured to inflate and contain the inhaling fluid received from the cartridge assembly in communication with the vaporizer, wherein the inflatable container is of a V-shape with a crescent overtop.

2. The inhalation system according to claim 1, wherein the fluid transfer member is a hose member comprising the open first end and an open second end, and wherein the hose member is configured to transfer the inhaling fluid received from the cartridge assembly in communication with the vaporizer to the mouth of the user via the mouthpiece operably connected to the open second end of the hose member.

3. The inhalation system according to claim 1, wherein the inhaling substance comprises a flavoring substance, and wherein, when the second opening of the valve member is connected to the vaporizer, the vaporizer is configured to heat the absorbent member with the flavoring substance accommodated in the cartridge to a temperature lower than a combustible temperature of the flavoring substance for vaporizing the flavoring substance and releasing a flavored fluid from the absorbent member into the fluid transfer member, wherein the absorbent member is positioned below the substance holder.

4. The inhalation system according to claim 3, wherein the flavoring substance is a first substance and comprises one or more flavors selected from a group comprising a fruit flavor and a secondary flavor, wherein the vaporizer is configured to vaporize a second substance, wherein the flavoring substance masks an aroma of vapors of the second substance.

5. The inhalation system according to claim 1, wherein the cartridge of the cartridge assembly comprises one or more inlet ports, a plurality of outlet ports, and a central opening, wherein the one or more inlet ports are positioned on an outer periphery of the cartridge, and wherein the plurality of outlet ports are positioned on an inner periphery of the cartridge.

6. The inhalation system according to claim 1, further comprising a locking member configured to lock the fluid transfer member to the valve member, wherein the locking member comprises a lock opening for inserting the open first end of the fluid transfer member, and wherein the locking member is configured to engageably connect the open first end of the fluid transfer member to the first opening of the valve member.

7. The inhalation system according to claim 1, wherein the valve member is configured to switch from a locked state to an unlocked state from an external computing device, wherein the valve member in the locked state acts as a barrier between the mouthpiece and the fluid transfer member, wherein the valve member in the unlocked state allows fluid communication between the mouthpiece and the fluid transfer member.

8. The inhalation system according to claim 7, wherein the inhalation system further comprises an identification element configured to be read by the external computing device for authentication of the user.

9. The inhalation system of claim 1, wherein the inhalation system further comprises the vaporizer, the vaporizer configured to vaporize a substance different from the inhaling fluid, such that vapors of the inhaling fluid mask an aroma of the second substance.

10. An inhalation system comprising:
   a fluid transfer member comprising an open first end configured to receive an inhaling fluid;
   a valve member operably connected to the open first end of the fluid transfer member, wherein the valve member comprises a body, a first opening, and a second opening, wherein the first opening is configured to be connected to the open first end of the fluid transfer member, and wherein the second opening is configured to be connected to a mouthpiece and a vaporizer;
   a cartridge assembly positioned within the body of the valve member, wherein the cartridge assembly comprises:
      a substance holder configured to contain an inhaling substance;
      an absorbent member positioned proximal to the substance holder, wherein the absorbent member is configured to absorb the inhaling substance received from the substance holder; and
      a cartridge configured to accommodate the substance holder and the absorbent member, wherein, when the second opening of the valve member is connected to the vaporizer, the vaporizer is configured to heat the absorbent member with the absorbed inhaling substance to a temperature lower than a combustible temperature of the inhaling substance for vaporizing the inhaling substance and releasing the inhaling fluid into the fluid transfer member; and
      the mouthpiece operably connected to the cartridge assembly via the second opening of the valve member, wherein the valve member is configured as one of a locking mouthpiece assembly and a non-locking mouthpiece, and wherein the valve member is configured to receive and transfer the inhaling fluid flowing from the fluid transfer member to a mouth of a user via the mouthpiece, and wherein the locking mouthpiece assembly is configured to allow authentication of the user prior to releasing the inhaling fluid to the mouth of the user via the mouthpiece;

wherein the valve member configured as the locking mouthpiece assembly comprises:

an enclosure comprising a first end and a second end;

a first flywheel built into the first end of the enclosure, wherein the first flywheel comprises passageways in fluid communication with the first opening of the valve member for allowing flow of the inhaling fluid from the fluid transfer member into the enclosure and out to the mouthpiece;

a stabilization pin attached to the first flywheel and positioned within the enclosure, the stabilization pin extending from the first flywheel to a tip of the mouthpiece, wherein the stabilization pin is configured with an inscribing scroll for inscribing a randomly generated bidirectional path and one or more identification elements thereon;

a second flywheel and a cylindrical member positioned coaxially around the stabilization pin and wherein the second flywheel and the cylindrical member are configured to operably communicate with each other for opening and closing the passageways of the first flywheel and controlling access to the inhaling fluid in the fluid transfer member;

the cylindrical member comprising track pins configured to navigate through the randomly generated bidirectional path along the inscribing scroll to unlock the valve member;

a display area positioned on the stabilization pin for displaying authentication elements along an X-axis and a Y-axis; and the mouthpiece operably connected to the second end of the enclosure and positioned proximal to the display area, wherein the mouthpiece is configured to receive and transfer the inhaling fluid flowing from the enclosure to the mouth of the user.

11. The inhalation system according to claim 10, further comprising tab elements positioned on one end of the second flywheel and on one end of the cylindrical member, wherein the tab elements of the second flywheel and the cylindrical member are in operable communication for opening and closing the passageways of the first flywheel.

12. The inhalation system according to claim 10, further comprising tab elements positioned on the cylindrical member for precluding the cylindrical member from moving a distance around the stabilization pin within the enclosure.

13. The inhalation system according to claim 10, wherein the enclosure of the valve member comprises a window configured to allow viewing of the authentication elements inscribed on the stabilization pin.

14. The inhalation system according to claim 10, wherein the one or more identification elements are configured to identify the inhalation system and are configured to be input into a mobile application deployed on a user device, and wherein the mobile application is in operable communication with an authentication server via a network for identifying the inhalation system and authenticating the user, and wherein the authentication server is configured to store identification information of the inhalation system and the user.

15. An inhalation system comprising:

a fluid transfer member comprising an open first end configured to receive an inhaling fluid;

a valve member operably connected to the open first end of the fluid transfer member, wherein the valve member comprises a body, a first opening, and a second opening, wherein the first opening is configured to be connected to the open first end of the fluid transfer member, and wherein the second opening is configured to be connected to a mouthpiece and a vaporizer;

a cartridge assembly positioned within the body of the valve member, wherein the cartridge assembly comprises:

a substance holder configured to contain an inhaling substance;

an absorbent member positioned proximal to the substance holder, wherein the absorbent member is configured to absorb the inhaling substance received from the substance holder; and a cartridge configured to accommodate the substance holder and the absorbent member, wherein, when the second opening of the valve member is connected to the vaporizer, the vaporizer is configured to heat the absorbent member with the absorbed inhaling substance to a temperature lower than a combustible temperature of the inhaling substance for vaporizing the inhaling substance and releasing the inhaling fluid into the fluid transfer member; and the mouthpiece operably connected to the cartridge assembly via the second opening of the valve member, wherein the valve member is configured as one of a locking mouthpiece assembly and the non-locking mouthpiece, and wherein the valve member is configured to receive and transfer the inhaling fluid flowing from the fluid transfer member to a mouth of a user via the mouthpiece, and wherein the locking mouthpiece assembly is configured to allow authentication of the user prior to releasing the inhaling fluid to the mouth of the user via the mouthpiece, wherein the substance holder and the cartridge are configured as ring-shaped members each comprising a central opening, and wherein the cartridge assembly further comprises:

a stem member configured to coaxially accommodate the cartridge with the substance holder through the central openings of the cartridge and the substance holder, wherein the stem member comprises an upper end and a lower end, and wherein the upper end of the stem member is connected to the open first end of the fluid transfer member, and wherein the lower end of the stem member is configured to be connected to the mouthpiece;

a cap member coaxially positioned on the stem member through a central opening of the cap member and suspended above the substance holder, wherein the cap member comprises pins extending downwardly from a lower surface of the cap member, and wherein the pins of the cap member are configured to puncture the substance holder and release the inhaling substance into the absorbent member accommodated in the cartridge, and wherein the pins of the cap member are further configured to plug the substance holder after puncturing the substance holder; and a collapsible spring member coaxially positioned on the stem member through a central opening of the collapsible spring member and positioned above the cap member, wherein the collapsible spring member is configured to push the cap member with the pins downwards towards the substance holder for puncturing the substance holder and releasing the inhaling substance into the absorbent member accommodated in the cartridge, and wherein the collapsible spring member is configured to create a funnel for harnessing the inhaling fluid into the fluid transfer member and preventing waste from dissipating while passing through the cartridge assembly.

16. The inhalation system according to claim 15, wherein the stem member is twistably removed from the body of the valve member prior to connecting the second opening of the valve member to the vaporizer.

17. The inhalation system according to claim 15, wherein the collapsible spring member is configured to collapse into a flat structure during compression to optimize space within the valve member.

18. An inhalation system comprising:
   a fluid transfer member comprising an open first end configured to receive an inhaling fluid;
   a valve member operably connected to the open first end of the fluid transfer member, wherein the valve member comprises a body, a first opening, and a second opening, wherein the first opening is configured to be connected to the open first end of the fluid transfer member, and wherein the second opening is configured to be connected to a mouthpiece and a vaporizer;
   a cartridge assembly positioned within the body of the valve member, wherein the cartridge assembly comprises:
      a substance holder configured to contain an inhaling substance;
      an absorbent member positioned proximal to the substance holder, wherein the absorbent member is configured to absorb the inhaling substance received from the substance holder; and
      a cartridge configured to accommodate the substance holder and the absorbent member, wherein, when the second opening of the valve member is connected to the vaporizer, the vaporizer is configured to heat the absorbent member with the absorbed inhaling substance to a temperature lower than a combustible temperature of the inhaling substance for vaporizing the inhaling substance and releasing the inhaling fluid into the fluid transfer member;
   the mouthpiece operably connected to the cartridge assembly via the second opening of the valve member, wherein the valve member is configured to receive and transfer the inhaling fluid flowing from the fluid transfer member to a mouth of a user via the mouthpiece;
   a stem member; and
   a pins member positioned downwards over the substance holder, the pins member operably coupled to the stem member, wherein pins member and the stem member are configured such that unscrewing the stem member from the valve member causes the pins member to puncture the substance holder resulting in release of the inhaling substance into the absorbent member, where pins of the pins member remain descended into the substance holder plugging holes created by puncturing.

19. The inhalation system according to claim 18, wherein the substance holder and the cartridge are ring shaped each with a central opening, wherein the stem member is configured to coaxially accommodate the cartridge with the substance holder through the respective central opening of the cartridge and the substance holder.

* * * * *